United States Patent [19]
Sugimoto et al.

[11] Patent Number: 5,545,587
[45] Date of Patent: Aug. 13, 1996

[54] POLYPEPTIDE POSSESSING CYCLOMALTODEXTRIN GLUCANOTRANSFERASE ACTIVITY

[75] Inventors: Toshiyuki Sugimoto; Michio Kubota; Shuzo Sakia, all of Okayama, Japan

[73] Assignee: Kabushiki Kaisha Hayashibara Seibutsu Kagaku Kenkyujo, Okayama, Japan

[21] Appl. No.: 145,514

[22] Filed: Nov. 4, 1993

Related U.S. Application Data

[62] Division of Ser. No. 794,347, Nov. 12, 1991, Pat. No. 5,278,059, which is a continuation of Ser. No. 438,993, Nov. 22, 1989, abandoned, which is a continuation of Ser. No. 804,487, Dec. 4, 1985, abandoned.

[51] Int. Cl.⁶ .................................................... C12P 19/18
[52] U.S. Cl. .......................... 435/97; 435/193; 536/23.2
[58] Field of Search .................... 435/97, 193; 536/23.2

[56] References Cited

U.S. PATENT DOCUMENTS

| 3,988,206 | 10/1976 | Shiosake | 195/62 |
| 4,219,571 | 8/1980 | Miyake | 426/48 |

*Primary Examiner*—Charles L. Patterson, Jr.
*Attorney, Agent, or Firm*—Browdy and Neimark

[57] ABSTRACT

The sequence of cyclomaltodextrin glucanotransferase (CGTase) gene derived from a microorganism of genus Bacillus and the amino acid sequence of CGTase are determined. A recombinant DNA carrying the CGTase gene is introduced by in vitro genetic engineering technique into a host microorganism of species *Bacillus subtilis* or *Escherichia coli*. The recombinant microorganism carrying the recombinant DNA autonomically proliferates to secrete a large amount of CGTase.

14 Claims, 16 Drawing Sheets

FIG. 5A

```
         10          20          30          40          50          60
GCTGGAAATC  TTAA TAAGGT  AAACT TTACA  TCAGATG TTG  TCTATCAAAT  TGTAGTGGAT 70          80          90         100         110         120
CGAT TTGTGG  ATGGAAATAC  ATCCAA TAAT  CCGAGTGGAG  CATTATTTAG  CTCAGGATGT 130         140         150         160         170         180
ACGA ATTTAC  GCAAGTATTG  CGGTGGAGAT  TGGCAAGGCA  TA TCAAT AA  AAT TAACGAT 190         200         210         220         230         240
GGGTAT TTAA  CAGATATGGG  TGTGACAGCG  ATAT GGATTT  CTCAGCCTGT  AGAAAATGTA 250         260         270         280         290         300
TT TTCTGTGA  TGAATGATGC  AAGCGGGTTCC  GCATCCTATC  ATGG TTATTG  GGCCGCGGAT 310         320         330         340         350         360
TTCAAAAAGC  CAAACCCGTT  TT TTGGTACC  CTCAGTGATT  TCCAACGTTT  AGTTGATGCC 370         380         390         400         410         420
GCACATGCAA  AAGGAATAAA  GGTAATTATT  GAC TTTGCCC  CCAACCATAC  TTCTCCTGCT 430         440         450         460         470         480
TCAGAAACGA  AT CCT TCTTA  TATGGAAAAC  GGACGACTGT  ACGATAATGG  GACATTGCTT 490         500         510         520         530         540
GGCGGTTACA  CAAATGATGC  CAACATGTAT  T TTCACCA TA  ACGGTGGAAC  AACGTTTCC
```

FIG. 5B

```
         550          560           570            580            590             600
AGCTT AGAGG  ATGGGATTA   TCGAAATCTG   TTTGACTTGG    CGGACCTTAA     CCATCAGAAC 610          620           630            640            650             660
CCTGT TA TTG  ATAGG TATTT  AAAAGATGCA  GTAAAAA TGT   GGA TAGATAT    GGGGATTGAT 670          680           690            700            710             720
GGTAT CCGTA  TGGATGCGGT   GAAGCACATG   CCGTTTG GAT   GGCAAAAATC     TCTGATGGAT 730          740           750            760            770             780
GAGAT TGATA   AC TATCGTCC  TGTCTTTACG  TT TGGGGAGT    GG TTTTGTC     AGAAAATGAA 790          800           810            820            830             840
GTGGACGCGA   ACAATCAT TA  CTTTGCCAAT   GAAAGTGG AA   TGAGT TTGCT    CGAT TTTCGT 850          860           870            880            890             900
TTCGGACAAA   AGCTTCGTCA   AGTATTGCGC   AATAACAGCG    ATAAT TGGTA    TGGC TTTAAT 910          920           930            940            950             960
CAAATGATTC   AAGATACGGC   ATCAGCATAT   GACGAGGTTC    TCG ATCAAGT    AACAT TCATA 970          980           990           1000           1010            1020
GACAACCATG   AT ATGGATCG  GTT TATGATT  GACGGAGGAG    ATCCGGCGCAA   GGTGGATATG 1030         1040          1050           1060           1070            1080
GCACTTGCTG   TA TTATTGAC  ATCCCGTGGC   GTACCGAA TA   T TACTATGG     TACAGAGCAA
```

FIG. 5C

```
     1090            1100            1110            1120            1130            1140
TACATGACCG      GTAACGGCGA      TCCAAACAAT      CGTAAGATGA      TGAGTTCATT      CAA TAAAAAT 1150            1160            1170            1180            1190            1200
ACTCGCGGCGT     ATCAAGT GAT     TCAAAAACTA      TCT TCTCTCC     GACGAAACAA      TCCGGCGTTA 1210            1220            1230            1240            1250            1260
GCT TATGGTG     ATACGGAACA      GCGTTGGATC      AATGGCGATG      TG TATGTGT A    TGAGCGACAG 1270            1280            1290            1300            1310            1320
T TTGGCAAAG     ATG TTGTGTT     AGTT CGGGTT     AATCGT AGTT     CAAGCAGTAA      TTAC TCGATT 1330            1340            1350            1360            1370            1380
ACTGGC TTAT     TTACAGCTTT      ACCAGCAGGA      ACATATACGG      ATCAGCT TGG     CGGTC TTTTA 1390            1400            1410            1420            1430            1440
GACGGAAATA      CAA TTCAAGT     CGGTTCAAAT      GGATCAGT TA     ATGCATT TGA     CTTAGGACCG 1450            1460            1470            1480            1490            1500
GGGGAAGTCG      GTGTATGGGC      ATACAGTGCA      ACAGAAAGCA      CGCCAATTAT      TGGTCATGT T 1510            1520            1530            1540            1550            1560
GGACCGATGA      TGGGCAAGT       CGGTCATCAA      GTAACCATTG      ATGGCGAAGG      ATTCGGAACA 1570            1580            1590            1600            1610            1620
AATACGGGCA      CTGTGAAGTT      CGGAACGACA      GCTGCCAATG      TTGTG TCT TG    GTCTAACAAT
```

FIG. 5D

```
1630       1640       1650       1660       1670       1680
CAAATCGTTG TGGCTGTACC AAATGTGTCA CCAGGAAAAT ATAAATATTAC CGTCCAATCA
1690       1700       1710       1720       1730       1740
TCAAGCGGTC AAACGAGTGC GGCTTATGAT AAC TTTGAAG TACTAACAAA TGATCAAGTG
1750       1760       1770       1780       1790       1800
TCAGTGCGGT TTGT TGTTAA TAACGCGACT ACCAATCTAG GGCAAAAA TAT ATACATTG TT
1810       1820       1830       1840       1850       1860
GGCAACGTAT ATGAGCTCGG CAACTGGGAC ACTAGTAAGG CAATCGGTCC AATGT TCAAT
1870       1880       1890       1900       1910       1920
CAAGTGGGT T ACTCCTATCC TACATGGTA T ATAGATGTCA GTGTCCCAGA AGGAAAGACA
1930       1940       1950       1960       1970       1980
ATT GAGTT TA AGT TTATTAA AAAAGACAGC CAAGGTAATG TCACTTGGGA AAGTGGTTCA
1990       2000       2010       2020       2030       2040
AATCATGT T T ATACGACACC AACGAATACA ACCGGAAAAA TTATAGTGGA TTGGCAGAAC
```

FIG. 6

```
         10          20          30          40          50          60
ATGAGAAGAT GGCTTTCGCT AGTCTTGAGC ATGTCATTTG TATTTAGTGC AATTTTTATA
         70          80          90         100
GTATCTGATA CGCAGAAAGT CACCGTTGAA GCA
```

FIG. 7

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| 1> Met | Arg | Arg | Trp | Leu | Ser | Leu | Val | Leu | Ser | Met | Ser | Phe | Val | Phe |
| 16> Ser | Ala | Ile | Phe | Ile | Val | Ser | Asp | Thr | Gln | Lys | Val | Thr | Val | Glu |
| 31> Ala | | | | | | | | | | | | | | |

FIG. 8A

|      | 1   | 2   | 3   | 4   | 5   | 6   | 7   | 8   | 9   | 10  | 11  | 12  | 13  | 14  | 15  |
|------|-----|-----|-----|-----|-----|-----|-----|-----|-----|-----|-----|-----|-----|-----|-----|
| 1>   | Ala | Gly | Asn | Leu | Asn | Lys | Val | Asn | Phe | Thr | Ser | Asp | Val | Val | Tyr |
| 16>  | Gln | Ile | Val | Val | Asp | Arg | Phe | Val | Asp | Gly | Asn | Thr | Ser | Asn | Asn |
| 31>  | Pro | Ser | Gly | Ala | Leu | Phe | Ser | Ser | Gly | Cys | Thr | Asn | Leu | Arg | Lys |
| 46>  | Tyr | Cys | Gly | Gly | Asp | Trp | Gln | Gly | Ile | Ile | Asn | Lys | Ile | Asn | Asp |
| 61>  | Gly | Tyr | Leu | Thr | Asp | Met | Gly | Val | Thr | Ala | Ile | Trp | Ile | Ser | Gln |
| 76>  | Pro | Val | Glu | Asn | Val | Phe | Ser | Val | Met | Asn | Asp | Ala | Ser | Gly | Ser |
| 91>  | Ala | Ser | Tyr | His | Gly | Tyr | Trp | Ala | Arg | Asp | Phe | Lys | Lys | Pro | Asn |
| 106> | Pro | Phe | Phe | Gly | Thr | Leu | Ser | Asp | Phe | Gln | Arg | Leu | Val | Asp | Ala |
| 121> | Ala | His | Ala | Lys | Gly | Ile | Lys | Val | Ile | Ile | Asp | Phe | Ala | Pro | Asn |
| 136> | His | Thr | Ser | Pro | Ala | Ser | Glu | Thr | Asn | Pro | Ser | Tyr | Met | Glu | Asn |
| 151> | Gly | Arg | Leu | Tyr | Asp | Asn | Gly | Thr | Leu | Leu | Gly | Gly | Tyr | Thr | Asn |
| 166> | Asp | Ala | Asn | Met | Tyr | Phe | His | His | Asn | Gly | Gly | Thr | Thr | Phe | Ser |
| 181> | Ser | Leu | Glu | Asp | Gly | Ile | Tyr | Arg | Asp | Leu | Phe | Asp | Leu | Ala | Asp |
| 196> | Leu | Asn | His | Gln | Asn | Pro | Val | Ile | Asp | Arg | Tyr | Leu | Lys | Met | Asp |
| 211> | Val | Lys | Met | Trp | Ile | Asp | Met | Gly | Ile | Asp | Gly | Ile | Ser | Met | Asp |
| 226> | Ala | Val | Lys | His | Met | Pro | Phe | Gly | Trp | Gln | Lys | Ser | Gly | Trp | Phe |
| 241> | Glu | Ile | Asp | Asn | Tyr | Arg | Pro | Val | Phe | Thr | Phe | Gly | Glu | Trp | Phe |
| 256> | Leu | Ser | Glu | Asn | Glu | Val | Asp | Ala | Asn | Asn | His | Tyr | Phe | Ala | Asn |
| 271> | Glu | Ser | Gly | Met | Ser | Leu | Leu | Asp | Phe | Arg | Phe | Gly | Gln | Lys | Leu |
| 286> | Arg | Gln | Val | Leu | Arg | Asn | Asn | Ser | Asp | Asn | Trp | Tyr | Gly | Phe | Asn |
| 301> | Gln | Met | Ile | Gln | Asp | Thr | Ala | Ser | Ala | Tyr | Asp | Glu | Val | Leu | Asp |
| 316> | Gln | Val | Thr | Phe | Ile | Asp | Asn | His | Asp | Met | Asp | Arg | Phe | Met | Ile |
| 331> | Asp | Gly | Gly | Asp | Pro | Arg | Lys | Val | Asp | Met | Ala | Leu | Ala | Val | Leu |
| 346> | Leu | Thr | Ser | Arg | Gly | Val | Pro | Asn | Ile | Tyr | Tyr | Gly | Thr | Glu | Gln |
| 361> | Tyr | Met | Thr | Gly | Asn | Gly | Asp | Pro | Ala | Asn | Arg | Lys | Met | Met | Ser |
| 376> | Ser | Phe | Asn | Lys | Asn | Thr | Arg | Ala | Tyr | Gln | Val | Ile | Gln | Lys | Leu |

FIG. 8B

| | | | | | | | | | | | | | | |
|---|---|---|---|---|---|---|---|---|---|---|---|---|---|---|
| 391> | Ser | Ser | Leu | Arg | Arg | Asn | Asn | Pro | Ala | Leu | Ala | Tyr | Gly | Asp | Thr |
| 406> | Glu | Gln | Arg | Trp | Ile | Asn | Gly | Asp | Val | Tyr | Val | Tyr | Glu | Arg | Gln |
| 421> | Phe | Gly | Lys | Asp | Val | Val | Val | Arg | Val | Asn | Arg | Ser | Ser | Ser | Ser |
| 436> | Ser | Asn | Tyr | Ser | Ile | Thr | Gly | Leu | Phe | Thr | Ala | Leu | Pro | Ala | Gly |
| 451> | Thr | Tyr | Thr | Asp | Gln | Leu | Gly | Val | Leu | Ala | Gly | Asn | Thr | Ile |
| 466> | Gln | Val | Gly | Ser | Asn | Gly | Ser | Val | Ala | Ala | Asp | Phe | Leu | Gly | Pro |
| 481> | Gly | Glu | Val | Gly | Val | Trp | Ala | Tyr | Met | Ser | Thr | Glu | Ser | Thr | Pro |
| 496> | Ile | Ile | Gly | His | Asp | Gly | Pro | Met | Gly | Met | Gly | Val | Gly | His | Gln |
| 511> | Val | Thr | Asp | Thr | Ala | Ala | Phe | Gly | Gly | Thr | Asn | Trp | Gly | Thr | Val |
| 526> | Lys | Phe | Thr | Val | Val | Gly | Ala | Asn | Val | Ser | Trp | Ser | Ser | Asn | Asn |
| 541> | Gln | Ile | Ala | Ser | Gln | Gly | Gln | Val | Ser | Pro | Gly | Lys | Lys | Tyr | Tyr |
| 556> | Ile | Thr | Gln | Ser | Leu | Asp | Asp | Gly | Ser | Ser | Ala | Ala | Arg | Tyr | Asp |
| 571> | Asn | Phe | Val | Leu | Thr | Thr | Asn | Asn | Thr | Val | Ile | Arg | Tyr | Phe | Val |
| 586> | Val | Asn | Ala | Glu | Asn | Thr | Leu | Val | Gln | Asp | Ser | Ile | Ile | Ala | Val |
| 601> | Gly | Asn | Val | Met | Tyr | Gly | Val | Trp | Asp | Thr | Tyr | Pro | Lys | Trp | Ile |
| 616> | Gly | Pro | Met | Phe | Asn | Asn | Ala | Leu | Tyr | Lys | Ser | Glu | Thr | Lys | Tyr |
| 631> | Ile | Asp | Ser | Ser | Pro | Val | Gly | Ser | Lys | Pro | Glu | Phe | His | Gly | Pro |
| 646> | Ile | Lys | Asp | Val | Gln | Gly | Asn | Val | Leu | Thr | Glu | Ile | Ala | Lys | Gly |
| 661> | Asn | His | Tyr | Ser | Ser | Thr | Asn | Thr | Thr | Pro | Arg | Thr | Trp | Lys | Ser |
| 676> | Val | Asp | Trp | Asn | Asn | Thr | Gly | Asn | Thr | Thr | Gly | Phe | Ile | Gly | Ile |

FIG. 9A

```
         10                 20                 30                 40                 50                 60
TCCCCGGATA CGAGCGGTGAA CAACAAGCTC AAT TTTAGCA CGGA TACGGT T TACCAGATT 70                 80                 90                100                110                120
GTAACCGACC GGTTTGTGGA CGGCAAT TCC GCCAACAACC CGACCGGAGC AGCCTTCAGC 130                140                150                160                170                180
AGCGGATCATT CCAACCTGAA GCTGTATTTC GGGGGCGGACT GGCAGGGGAT CACGAACAAA 190                200                210                220                230                240
ATCAACGACG GCTATCTGAC CGGAATGGGC ATCACCGCCC TCTGGA TCTC GCAGCCGGTT 250                260                270                280                290                300
GAGAACATCA CCGCCGTCAT CAATTA TTCG GGCGTCAACA ATACAG CTTA CC ACGGTTAC 310                320                330                340                350                360
TGGCCTCGCG ACTTCAAGAA GACCAATGCC GCGTTCGGCA GCTTCACCGA CT TC TCCAAT 370                380                390                400                410                420
TTGATCGCCG CAGCGCATTC ACACAATATC AAGGTAGT TA TGGACTT TGC ACCT AATCAC 430                440                450                460                470                480
ACCAACCCGG CTTCGAGTAC GGACCCCTCG TTCGCCGAGA ACGGCGCGCT CTACAACAAC 490                500                510                520                530                540
GGAACGCTGC TCGGCAAGTA TAGCAACGAT ACCGCCGGCC TG TTCCACCA CAATGGGCGGC
```

FIG. 9B

```
550         560         570         580         590         600
ACCGAT TTC T CGACGACTGA AAGCGGTATC TACAAGAACC TGTACGATCT CGGGGATATC
610         620         630         640         650         660
AATCAGA ACA ACAACACCAT CGACTCGTAT CTCAAGGAAT CGATCCAGCT GTGGCTGAAT
670         680         690         700         710         720
CTCGGAGTCG ACGGCATCCG CTTCGACGCC GTGAAGCATA TGCCTCAGGG CTGGCAGAAG
730         740         750         760         770         780
AGCTACGTCT CGTCGATCTA CAGCAGCGCC AATCCGGTGT TCACC TTCGG TGAATGGTTC
790         800         810         820         830         840
CTCGGGCCCG ACGAAAATGAC CCAGGACAAC ATCAACTTCG CGAATCAGAG CGGCATGCAC
850         860         870         880         890         900
CTGCTG GACT TTGCGTTTGC GCAGGAAATC CGTGAAGTGT TCCGGCGACAA GTCGGAGACG
910         920         930         940         950         960
ATGACCGACC TGAACTCGGT GATCTCCAGC ACCGGCTCCA GCTATAA TTA CATCAACAAC
970         980         990         1000        1010        1020
ATGG TTACGT TCATCGACAA CCATGACACA TG GACCGCTTCC AGCAAGCCGG AGCGAGCACT
1030        1040        1050        1060        1070        1080
CGCCCGACCG AGCAGGCTCT TGCGGTAACG CTGACTTCCC GCGGCGTTCC GGCAATCTAC
```

FIG. 9C

```
1090          1100           1110           1120           1130           1140
TACGGTACAG    AGCAA TATAT    GACCGGGCAAC    GGCGACCCGA    ACAACCGCGG     CATGATGACC 1150          1160           1170           1180           1190           1200
GGCTTCGATA    CGAACAAGAC     AGCGTACAAA     GT GATCAAGG   CGCTGGCTCC     GCTTCGCAAG 1210          1220           1230           1240           1250           1260
TCCAACCCGG    CTCTCGCCTA     CGGCTCGACG     AC CCAGCGTT   GGGTGAACAG     CGACGTCTAC 1270          1280           1290           1300           1310           1320
GTAT ATGAAC   GCAAGTTCGG     AAGCAACGTA     GC T TTCGTTG  CCGTCAACCG     CAGCTCGACG 1330          1340           1350           1360           1370           1380
ACTGCCT ATC   CGATATCGGG     AGCGC TTACT    GC TCTGCCAA   ACGGAACGTA     TACCGACGTT 1390          1400           1410           1420           1430           1440
CTCGGCGGCC    TGC TTAATGG    CAATT CAATT    AC CGTTAACG   GCGGCACGGT     CAGCAA CTTT 1450          1460           1470           1480           1490           1500
ACACT TGCAG   CGGGCGGGTAC    GGCAGTCTGG     CAGTACACGA    CGACGGAATC     CTCGCC GATT 1510          1520           1530           1540           1550           1560
ATCGGCAACG    TCGGCCCGAC     TATGGGCAAG     CCCGGCAACA    CCATCACGAT     CGACGGACGC 1570          1580           1590           1600           1610           1620
GGCTT CGGTA   CTACGAAGAA     CAAAGTT ACT T TCGGTACGA     CAGCCGTAC      CGGCGGCAAC
```

FIG. 9D

| | | | | |
|---|---|---|---|---|
| 1630 ATCGTGAGCT | 1640 GGGAAGATAC | 1650 CGAAATCAAG | 1660 GTCAAAGTTC | 1670 CGAACGTGGC | 1680 CGCCGGCAAC |
| 1690 ACGGCCGTTA | 1700 CGGTAACGAA | 1710 CGCCGCCGGC | 1720 ACTACCAGCG | 1730 CAGCGTTCAA | 1740 CAACTTTAAC |
| 1750 GTACTGACTG | 1760 CCGATCAGGT | 1770 CACTGTCCGC | 1780 TTCAAAGTCA | 1790 ACAATGCCAC | 1800 CACGGCCCTG |
| 1810 GGACAAAACG | 1820 TCTACCTGAC | 1830 CGGTAACGTC | 1840 GCCGAGCTTG | 1850 GCAACTGGAC | 1860 AGCCGCCAAC |
| 1870 GCAATCGGTC | 1880 CGATGTACAA | 1890 CCAGGTAGAA | 1900 GCCAGCTATC | 1910 CGACTTGGTA | 1920 CTTCGACGTC |
| 1930 AGCGTTCCGG | 1940 CCAACACGGC | 1950 GCTGCAATTC | 1960 AAGTTCATCA | 1970 AAGTGAACGG | 1980 CTCGACAGTG |
| 1990 ACTTGGGAAG | 2000 GCGGCAACAA | 2010 CCACACCTTC | 2020 ACCTCGCCTT | 2030 CGAGCGGGCGT | 2040 TGCGACCGTA |
| 2050 ACGGTCGATT | 2060 GGCAGAAC | | | | |

FIG. 10

```
         10         20         30         40         50         60
ATGAAAAAGC AAGTCAAATG GTTGACGTCG GTGTCGATGT CCGTAGGGAT CGCACTCGGC
         70         80         90
GCGGCGCTGC CTGTATGGGC A
```

FIG. 11

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Met | Lys | Lys | Gln | Val | Lys | Trp | Leu | Thr | Ser | Val | Ser | Met | Ser | Val |
| 16> | Gly | Ile | Ala | Leu | Gly | Ala | Ala | Leu | Pro | Val | Trp | Ala | | | |

```
391> Val Ile  Lys Ala Leu Ala  Pro Leu Arg Lys Ser Asn Pro Ala Leu
406> Ala Tyr  Gly Ser Thr Thr  Gln Arg Trp Val Asn Ser Asp Val Tyr
421> Val Tyr  Glu Arg Phe Lys  Asn Ser Asn Ala Leu Ala Val Ala Val
436> Asn Arg  Ser Ser Thr Thr  Ala Tyr Pro Ile Ser Gly Val Leu Thr
451> Ala Leu  Pro Asn Gly Gly  Tyr Thr Asp Val Gly Ala Gly Leu Leu
466> Asn Gly  Asn Ala Ile Gly  Val Thr Gly Gly Val Ser Asn Asn Phe
481> Thr Leu  Ala Ser Thr Gly  Gly Ile Val Trp Gln Tyr Thr Thr Thr
496> Glu Ser  Pro Thr Phe Thr  Ile Gly Arg Gly Pro Gly Met Gly Lys
511> Pro Gly  Asn Pro Asp Phe  Thr Thr Ala Arg Gly Phe Gly Gly Thr
526> Lys Asn  Lys Thr Glu Asp  Ile Val Lys Thr Val Thr Gly Ala Asn
541> Ile Val  Ser Ala Val Thr  Ala Thr Val Asn Val Thr Ala Pro Asn
556> Val Ala  Ala Gly Gly Phe  Asn Asn Ala Asn Leu Thr Ala Ala Asp
571> Thr Thr  Thr Ser Ala Arg  Phe Phe Lys Thr Val Leu Thr Leu Leu
586> Gln Val  Ser Thr Val Tyr  Leu Ala Asn Thr Ala Ala Glu Gln Asn
601> Gly Gln  Asn Ala Val Tyr  Ala Ile Gly Met Tyr Val Asn Gly Asn
616> Trp Thr  Pro Gln Leu Trp  Arg Asp Pro Val Ser Tyr Gly Val Leu
631> Ala Ser  Ala Tyr Pro Gly  Phe Lys Lys Val Ala Gln Thr Ala Asn
646> Thr Leu  Leu Leu Asn Phe  Ile Asn Lys Asn Ser Asn Pro Ser Glu
661> Thr Ala  Gly Glu Phe Gly  Asn His Thr Phe Thr Gly Pro Thr Val
676> Gly Val  Ala Ala Val Thr  Asp Gln Asn Asn Asn Ser Ser. Ser
``` ained. 5,545,587

POLYPEPTIDE POSSESSING CYCLOMALTODEXTRIN GLUCANOTRANSFERASE ACTIVITY

CROSS-REFERENCE TO RELATED APPLICATIONS

This application is a division of application Ser. No. 07/794,347, filed Nov. 12, 1991, now U.S. Pat. No. 5,278,059 which is a continuation of application Ser. No. 07/438,993, filed Nov. 22, 1989, now abandoned which was a continuation of application Ser. No. 06,804,487, filed Dec. 4, 1985, now abandoned.

FIELD OF THE INVENTION

The present invention relates to a polypeptide, and particularly a polypeptide possessing cyclomaltodextrin glucanotransferase activity. The present invention also relates to DNA, microorganisms and processes related to the production of such polypeptide.

ABBREVIATIONS

Throughout the present specification and claims, amino acids, peptides, etc., are designated with abbreviations which are commonly used in the art. Examples of such abbreviations are as follows.

When optical isomers are possible, the abbreviations of amino acids mean L-isomers, unless specified otherwise.

DNA is the abbreviation of deoxyribonucleic acid; RNA ribonucleic acid; A, adenine; T, thymine; G, guanine; C, cytosine; dNTP, deoxynucleotide triphosphate; ddNTP, dideoxynucleotide triphosphate; dCTP, deoxycytidin triphosphate; SDS, sodium dodecyl sulfate; Ala, alanine; Arg, arginine; Asn, asparagine; Asp, aspartic acid; Cys, cysteine; Gln, glutamine; Glu, glutamic acid; Gly, glycine; His, histidine; Ile, isoleucine; Leu, leucine; Lys, lysine; Met, methionine; Phe, phenylalanine; Pro, proline; Ser, serine; Thr, threonine; Trp, tryptophan; Tyr, tyrosine; Val, valine; and CGTase, cyclomaltodextrin glucanotransferase.

The wording of "polypeptide" means "polypeptide possessing CGTase activity".

DESCRIPTION OF THE PRIOR ART

CGTase, or macerans has been known for years as an enzyme produced by *Bacillus macerans*.

Recently, it was found that CGTase is produced by other microorganisms such as those of species *Bacillus stearothermophilus* and *Bacillus circulans*. The saccharide transfer activity of CGTase now has many industrial uses.

For example, cyclodextrins are produced by subjecting gelatinized starch to the action of CGTase, while glycosylsucrose production utilizes the saccharide transfer reaction from starch to sucrose which is effected by subjecting a mixture solution of liquefied starch and sucrose to CGTase.

Cyclodextrins are now expanding as a host for forming stable inclusion complexes with organic compounds which are volatile or susceptible to oxidation. Demand for glycosylsucrose is also expanding as a mildly-sweet low-cariogenic sweetener which is commercialized by Hayashibara Co., Ltd., Okayama, Japan, under the Registered Trademark of "Coupling Sugar".

In order to meet these demands, development of means to provide a constant CGTase supply is an urgent necessity. This requires determination of the amino acid sequence of the polypeptide that possesses CGTase activity.

Such amino acid sequence has, however, so far been unknown.

BRIEF DESCRIPTION OF THE ACCOMPANYING DRAWINGS

Figure 1:
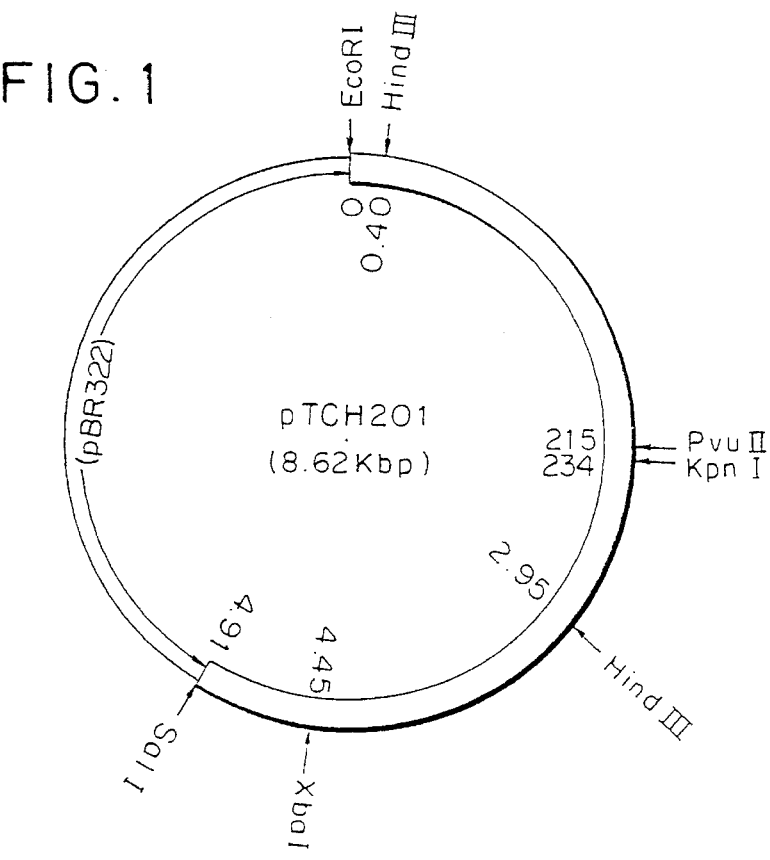
FIG. 1 shows the restriction map of recombinant DNA pTCH201, in particular that of the DNA fragment which carries the polypeptide gene derived from *Bacillus stearothermophilus*.

FIG. 5 (which is FIGS. 5A–5D, collectively) shows the nucleotide sequence of the polypeptide gene derived from *Bacillus stearothermophilus*.

FIG. 6 shows the nucleotide sequence of the signal peptide gene located upstream of the 5'-terminal end of the polypeptide gene of FIG. 5.

FIG. 7 shows the amino acid sequence of the signal peptide of FIG. 6.

FIG. 8 (which is FIGS. 8A–8B, collectively) shows the amino acid sequence of the polypeptide determined with reference to the sequence shown in FIG. 5.

FIG. 9 (which is FIGS. 9A–9D, collectively) shows the nucleotide sequence of the polypeptide gene derived from *Bacillus macerans*.

FIG. 10 shows the sequence of the signal peptide located upstream of the 5'-site of the polypeptide of FIG. 9.

FIG. 11 shows the amino acid sequence of the signal peptide of FIG. 10.

Figure 12A:
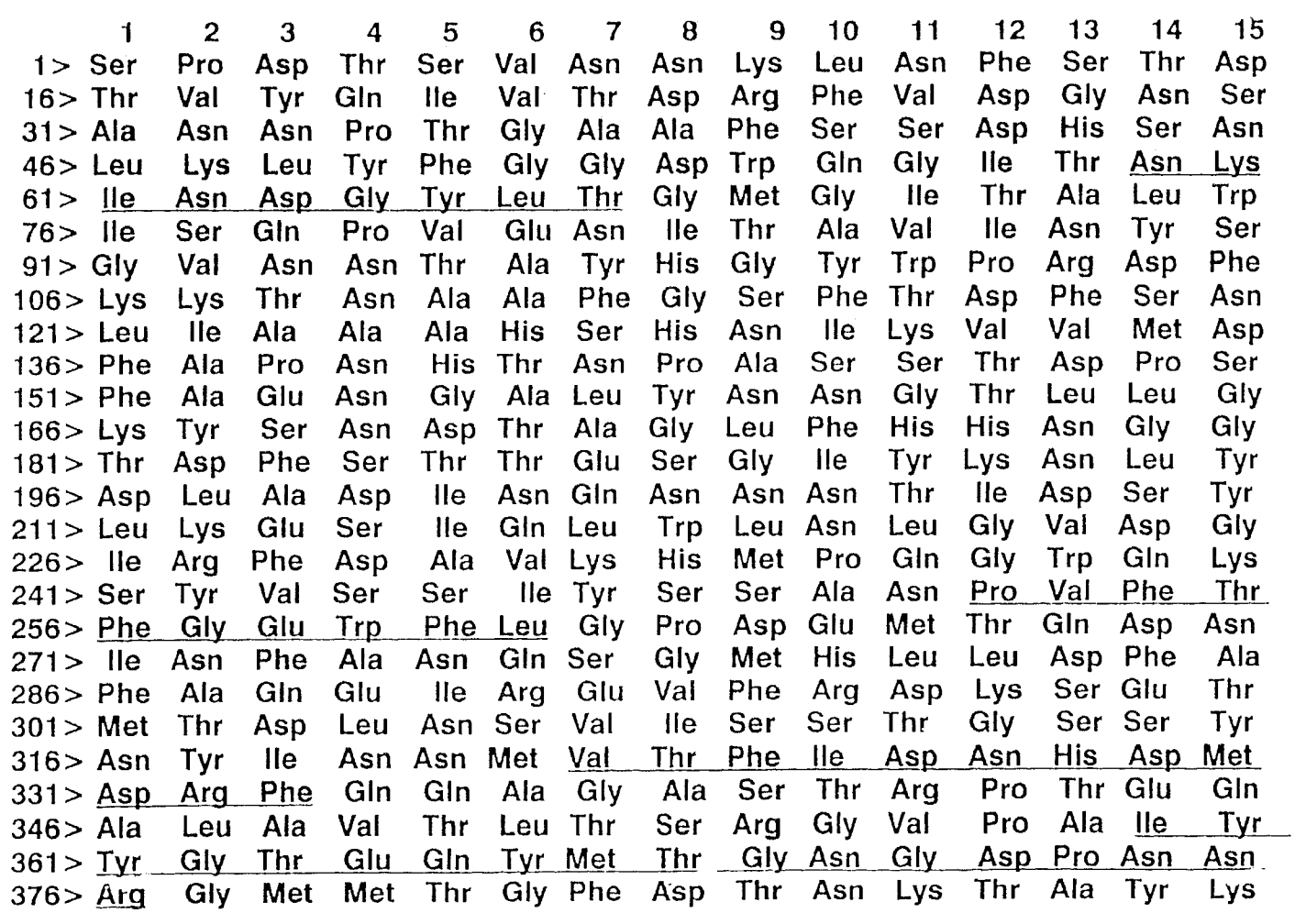

FIG. 12 (which is FIGS. 12A–12B, collectively) shows the amino acid sequence of the polypeptide derived from *Bacillus macerans*.

SUMMARY OF THE INVENTION

The present inventors carried out investigations to determine the amino acid sequence of CGTase polypeptide; to assure a wide polypeptide availability by recombinant gene technology; and also to improve polypeptide productivity.

As a result, the present inventors found that the CGTase polypeptide comprises one or more partial amino acid sequences selected from the group consisting of
(a) Asn-Lys-Ile-Asn-Asp-Gly-Tyr-Leu-Thr,
(b) Pro-Val-Phe-Thr-Phe-Gly-Glu-Trp-Phe-Leu,
(c) Val-Thr-Phe-Ile-Asp-Asn-His-Asp-Met-Asp-Arg-Phe,
(d) Ile-Tyr-Tyr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly,
and that, more particularly, these partial amino acids sequences (a), (b), (c), (d) and (e) are located in order of nearness to the N-terminal end of the polypeptide.

The polypeptide is characterized by the facts that it forms cyclodextrin from soluble starch; that it shows a molecular weight of 70,000±10,000 daltons on SDS-polyacrylamide electrophoresis; and that it has a specific activity of 200±30 units/mg protein.

The present inventors also found that polypeptides derived from *Bacillus stearothermophilus* and *Bacillus macerans* have the amino acid sequences as shown in FIGS. 8 and 12, respectively. Both amino acid sequences will be discussed hereafter.

In addition, the present inventors determined the amino acid sequences of the signal peptides which regulate polypeptide secretion from producer microorganisms.

The present invention and features thereof will hereinafter be explained.

DESCRIPTION OF THE PREFERRED EMBODIMENTS

In the present invention, the amino acid sequence of the CGTase polypeptide is determined by cloning the polypeptide gene from a CGTase producer microorganism and sequencing the polypeptide gene.

The amino acid sequence containing N-terminal end is determined by analyzing a highly-purified polypeptide with a gas-phase protein sequencer.

Cloning of the Polypeptide Gene

In the present invention, a DNA fragment, obtained by separating DNA from a donor microorganism capable of producing the polypeptide and digesting the DNA, for example with ultrasound or restriction enzymes, and a vector fragment, obtained by cleaving a vector in the same way, are ligated, for example with DNA ligase, to obtain a recombinant DNA carrying the polypeptide gene.

The donor microorganism is chosen from bacteria which produce the polypeptide. Examples of such bacteria are those of genus Bacillus such as *Bacillus macerans, Bacillus megaterium, Bacillus circulans, Bacillus polymyxa,* and *Bacillus stearothermophilus,* and those of genus Klebsiella such as *Klebsiella pneumoniae,* as described, for example, in Japan Patent Kokai No. 20,373/72, Japan Patent Kokai No. 63,189/75, Japan Patent Kokai No. 88,290/75, and Hans Bender, *Archives of Microbiology,* Vol. 111, pp. 271–282 (1977).

Recombinant microorganisms in which polypeptide producibility has been introduced by genetic engineering techniques can also be used as the donor microorganism.

The DNA of the donor microorganism can be prepared by culturing the donor microorganism, for example with a liquid culture medium for about 1–3 days under aeration-agitation conditions, centrifugally collecting the microorganism from the culture, and lysing the microorganism. Examples of bacteriolytic procedures are cytohydrolysis using lysozyme or β-glucanase, and ultrasonic treatment.

Other enzymes, such as protease, and/or surface active agents, such as sodium lauryl sulfate, can be used in combination, if necessary. Of course, freezing-thawing treatment can be carried out, if necessary.

In order to isolate DNA from the resultant lysate, two or more conventional procedures, such as phenol extraction, protein removal, protease treatment, ribonuclease treatment, alcohol sedimentation, and centrifugation, are combined.

Although DNA ligation can be effected by treating DNA- and vector-fragments, for example with ultrasound or restriction enzymes, it is desirable to use restriction enzymes, particularly those acting specifically on a prescribed nucleotide sequence, for smooth ligation. Specifically suited are Type II restriction enzymes, for example, EcoRI, HindIII, BamHI, SalI, SlaI, XmaI, MboI, XbaI, SacI, PstI, etc.

Bacteriophages and plasmids which autonomically proliferate in the host microorganism are suitable for vectors.

When a microorganism of species *Escherichia coli* is used as the host, bacteriophages such as λgt·λc and λgt·λB are employable, while p11, ψ1 and ψ105 are usable when a microorganism of species *Bacillus subtilis* is used as the host.

As regards plasmids, when a microorganism of species *Escherichia coli* is used as the host, plasmids such as pBR322 and pBR325 are employable, while pUB110, pTZ4 (pTP4) and pC194 are usable for a host microorganism of species *Bacillus subtilis*. Plasmids which autonomically proliferate in two or more different host microorganisms, for example, pHV14, TRp7, YEp7 and pBS7, can be used as the vector. These vectors are cleaved with the same types of restriction enzymes as used in DNA digestion to obtain a vector fragment.

DNA- and vector-fragments are ligated with conventional procedures using DNA ligase. For example, DNA- and vector-fragments are first annealed, then subjected in vitro to the action of a suitable DNA ligase to obtain a recombinant DNA. If necessary, such recombinant DNA can be prepared by introducing the annealed fragments into the host microorganism to subject them to in vivo DNA ligase.

The host microorganisms usable in the invention are those in which recombinant DNA autonomically and consistently proliferates to express its characteristics. Specifically, microorganisms which are not capable of producing α-amylase (EC 3.2.1.1) are preferably used because the use of such microorganisms facilitates isolation and purification of the secreted polypeptide.

The recombinant DNA can be introduced into the host microorganism with any conventional procedure. For example, when the host microorganism belongs to the species *Escherichia coli*, introduction of recombinant DNA is effected in the presence of calcium ion, while the competent cell- and protoplast-methods are employed when a host microorganism of genus Bacillus is used.

The recombinant microorganism in which recombinant DNA has been introduced is selected by collecting clones which grow on plate culture containing starch to convert the starch into cyclodextrin.

The present inventors found that the recombinant DNA carrying the polypeptide gene cloned in this way can be easily introduced, after isolation from the recombinant microorganism, into a different host microorganism. It was also found that a DNA fragment carrying the polypeptide gene, obtained by digesting a recombinant DNA carrying the gene with restriction enzymes, can be easily ligated with a vector fragment which has been obtained in the same manner.

Furthermore, the present inventors found that the polypeptide gene in the recombinant DNA obtained according to the present invention is cleaved by restriction enzyme PvuII, purchased from Toyobo Co., Ltd., Osaka, Japan, to lose the ability of expressing the polypeptide gene because the recombinant DNA has a PvuII restriction cleavage site.

Sequence of the Polypeptide Gene

The polypeptide gene is sequenced by the chain-terminator method as described in *Gene*, Vol. 9, pp.259–268 (1982).

This method contains the step of inserting a cloned DNA fragment carrying the polypeptide gene into the insertion site of a suitable plasmid such as pUC18 using restriction enzymes. The obtained recombinant plasmid is introduced by transformation into a suitable *Escherichia coli* strain such as *Escherichia coli* JM83, followed by selection of the recombinant microorganism that contains the plasmid.

The recombinant plasmid is prepared from the proliferated recombinant microorganism.

The obtained recombinant plasmid is annealed together with a synthetic primer, and the Klenow fragment is then allowed to act on the mixture to extend the primer, as well as to form the complementary DNA.

Thereafter, the mixture is subjected sequentially to polyacrylamide-electrophoresis and radioautography, followed by sequencing of the polypeptide gene.

The signal polypeptide which regulates polypeptide secretion from the cell is sequenced in the same manner.

Amino Acid Sequence of the Polypeptide

The amino acid sequence of the polypeptide is determined from the DNA sequence of the polypeptide gene.

The amino acid sequence of the signal peptide is determined in the same manner.

N-terminal Amino Acid Sequence of the Polypeptide

A polypeptide producer microorganism of genus Bacillus is cultured with a nutrient culture medium to produce the polypeptide. The supernatant, centrifugally obtained from the culture, is purified by ammonium sulfate fractionation, ion exchange chromatography and high-performance liquid chromatography to obtain a high-purity polypeptide specimen. The specimen is then degraded with a gas-phase protein sequencer in accordance with the method described in *Journal of Biological Chemistry*, Vol. 256, pp. 7990–7997 (1981), and isolated with high-performance liquid chromatography, followed by determination of the partial amino acid sequence of the N-terminal end.

Preparation of Polypeptide with Recombinant Microorganism

The present inventors found that a large amount of polypeptide can be consistently produced by culturing a recombinant microorganism with a nutrient culture medium.

To the nutrient culture medium is incorporated, for example, a carbon source; a nitrogen source, minerals, and, if necessary, small amounts of organic nutrients such as amino acids and vitamins.

Starch, partial starch hydrolysate, and saccharides such as glucose, fructose and sucrose are suitable for the carbon source. Inorganic nitrogen sources such as ammonia gas, ammonia water, ammonium salts and nitrates; organic nitrogen sources such as peptone, yeast extract, and defatted soybean, corn steep liquor and meat extract are suitable for the nitrogen source.

The recombinant microorganism is cultured with a nutrient culture medium for about 1–4 days under aeration-agitation conditions to accumulate polypeptide while keeping the culture medium, for example, at pH 4–10 and 25°–65° C.

Although the polypeptide in the culture may be used intact, generally the culture is separated into polypeptide solution and cells with conventional procedures such as filtration and centrifugation, prior to its use.

When the polypeptide is present in the cells, the cells are first treated with ultrasound, surface active agent and/or cytohydrolysis, then with filtration and centrifugation to separate a solution containing the polypeptide.

The solution containing the polypeptide thus obtained is purified, for example by combination of concentration in vacuo, concentration using a membrane filter, salting-out using ammonium sulfate or sodium sulfate, fractional sedimentation using methanol, ethanol or acetone, to obtain a highly-purified polypeptide specimen which is advantageously usable as industrial polypeptide material.

To further improve the quality of the polypeptide, the amino acid sequence of the polypeptide may be partially substituted, removed, added, or modified in such a manner that are polypeptide does not lose its CGTase activity prior to its use.

One unit of CGTase activity is defined as the amount of polypeptide that diminishes completely the iodine-coloration of 15 mg soluble starch at 40° C. over a period of 10 minutes under the following reaction conditions: To 5 ml of 0.3 w/w % soluble starch solution containing 0.02M acetate buffer (pH 5.5) and $2\times10^{-3}$M calcium chloride is added 0.2 ml of a diluted enzyme solution, and the mixture is incubated at 40° C. for 10 minutes. Thereafter, 0.5 ml of the reaction mixture is sampled and 15 ml of 0.02N aqueous sulfuric acid solution is added to suspend the enzymatic reaction. To the reaction mixture 0.2 ml of 0.1N $I_2$-KI solution is added to effect coloration, and its absorbance at a wavelength of 660 nm is determined.

Deposition of Recombinant Microorganisms

Recombinant microorganisms *Escherichia coli* TCH201, *Escherichia coli* MAH2, *Bacillus subtilis* MAU210, and *Bacillus subtilis* TCU211 have been deposited under the accession numbers of FERM BP-2109, BP-2110, BP-2111, and BP-2112, respectively, at the Fermentation Research Institute, Agency of Industrial Science and Technology, 1–3, Higashi 1 chome, Yatabemachi, Tsukuba-gun, Ibaraki-ken, Japan.

Several embodiments according to the present invention are disclosed in the following examples:

EXAMPLE 1

Cloning of *Bacillus stearothermophilus* Polypeptide Gene into *Escherichia coli*

Preparation of Chromosome DNA Carrying the Heat-Resistant-Polypeptide Gene of *Bacillus stearothermophilus*

The chromosome DNA carrying the heat-resistant-polypeptide gene of *Bacillus stearothermophilus* was prepared in accordance with the method described by Saito and Miura, *Biochimica et Biophisica Acta*, Vol. 72, pp. 619–629 (1963). A seed culture of *Bacillus stearothermophilus* FERM-P No. 2225 was cultured with brain heart infusion medium at 50° C. overnight under vigorous shaking conditions. The cells, centrifugally collected from the culture, were suspended with TES buffer (pH 8.0) containing Tris-aminomethane, hydrochloric acid, EDTA and sodium chloride, mixed with 2 mg/ml of lysozyme, and incubated at 37°

C. for 30 minutes. The incubated mixture was frozen, allowed to stand at −20° C. overnight, mixed with TSS buffer (pH 9.0) containing Tris-aminomethane, hydrochloric acid, sodium lauryl sulfate and sodium chloride, heated to 60° C., mixed with a mixture of TES buffer (pH 7.5) and phenol (1:4 by volume), cooled in ice-chilled water, and centrifuged to obtain a supernatant. To the supernatant was added two volumes of cold ethanol to recover a crude chromosomal DNA which was then dissolved in SSC buffer (pH 7.1) containing sodium chloride and trisodium citrate; thereafter, the mixture was subjected to both "RNase A", a ribonuclease commercialized by Sigma Chemical Co., Mo., USA, and "Pronase E", a protease commercialized by Kaken Pharmaceutical Co., Ltd., Tokyo, Japan, mixed with a fresh preparation of TES buffer and phenol mixture, cooled, centrifuged, and mixed with two volumes of cold ethanol to recover a purified chromosomal DNA. The chromosomal DNA was dissolved in a buffer (pH 7.5) containing Tris-aminomethane, hydrochloric acid and EDTA, and stored at −20° C.

EXAMPLE 1-(2)

Preparation of Plasmid pBR322

Plasmid pBR322 (ATCC 37013) was isolated from *Escherichia coli* in accordance with the method described by J. Meyer et al. in *Journal of Bacteriology*, Vol. 127, pp. 1524–1537 (1976).

EXAMPLE 1-(3)

Preparation of Recombinant DNA Carrying Polypeptide Gene

The purified chromosomal DNA carrying the heat-resistant-polypeptide gene, prepared in Example 1-(1), was partially digested with restriction enzyme MboI, purchased from Nippon Gene Co., Ltd., Toyama, Japan to give DNA fragments of 1–20 kbp. Separately, the pBR322 specimen, prepared in Example 1-(2), was completely cleaved with restriction enzyme BamHI, purchased from Nippon Gene Coo, Ltd., and the cleaved product was subjected to *Escherichia coli* alkaline phosphatase, purchased from Takara Shuzo Co., Ltd., Kyoto, Japan, to prevent self-ligation of the plasmid fragment as well as to dephosphorize the 5'-terminal end of the fragment.

Both fragments were then ligated by subjecting them to $T_4$ DNA ligase, purchased from Nippon Gene Co., Ltd., at 4° C. overnight to obtain a recombinant DNA.

EXAMPLE 1-(4)

Introduction of Recombinant DNA into *Escherichia coli*

*Escherichia coli* HB101 (ATCC 33694), a strain incapable of producing amylase, was used as the host.

The microorganism was cultured with L-broth at 37° C. for 4 hours, and the cell, centrifugally collected from the culture, was suspended with 10 mM acetate buffer (pH 5.6) containing 50 mM manganese chloride, centrifugally collected again, resuspended with 10 mM acetate buffer (pH 5.6) containing 125 mM manganese chloride, mixed with the recombinant DNA prepared in Example 1-(3), and allowed to stand in an ice chilled water bath for 30 minutes. The mixture was then warmed to 37° C., mixed with L-broth, spread on L-broth agar plate medium containing 50 µg/ml of ampicillin and 2 mg/ml starch, and incubated at 37° C. for 24 hours to form colonies.

The colonies which had degraded the starch into cyclodextrin were selected by the iodine-coloration method. Thus, the microorganisms in which the recombinant DNA carrying polypeptide gene had been introduced were selected. A recombinant microorganism was then proliferated, and the recombinant DNA was extracted from the proliferated microoryganism by the plasmid preparation method in Example 1-(2), subjected to restriction enzymes to determine the restriction cleavage sites; and completely digested with restriction enzyme EcoRI purchased from Nippon Gene Co., Ltd. The digested product was subjected to $T_4$ DNA ligase similarly as in Example 1-(3) to obtain a recombinant DNA, followed by selection of a recombinant microorganism in accordance with the method in Example 1-(4). The recombinant microorganism contained a recombinant DNA of a relatively small-size that carries no polypeptide gene.

The recombinant DNA and plasmid pBR322 were then completely digested with restriction enzyme SalI, purchased from Nippon Gene Co., Ltd., and treated similarly as in the case of EcoRI to select recombinant microorganisms containing a recombinant DNA of a much smaller-size that carries the polypeptide gene.

One of these microorganisms and its recombinant DNA were named as "*Escherichia coli* TCH201 (FERM BP-2109)" and "pTCH201".

The restriction map of recombinant DNA pTCH201, in particular that of the DNA fragment derived from *Bacillus stearothermophilus* microorganism, is as shown in FIG. 1.

FIG. 1 clearly shows that the DNA fragment carrying the polypeptide gene derived from *Bacillus stearothermophilus* microorganism is cleaved by either restriction enzyme PvuII purchased from Toyobo Co., Ltd., KpnI, HindIII purchased from Nippon Gene Co., Ltd., or XbaI purchased from Takara Shuzo Co., Ltd, but not by EcoRI, BamHi, PstI, XhoI, BglII or AccI, all purchased from Nippon Gene Co., Ltd.

EXAMPLE 2

Cloning of Polypeptide Gene of *Bacillus stearothermophilus* into *Bacillus subtilis*

EXAMPLE 2-(1)

Preparation of Recombinant DNA pTCH201

Recombinant DNA pTCH201 was isolated from *Escherichia coli* TCH201 (FERM BP-2109) in accordance with the method in Example 1-(2).

EXAMPLE 2-(2)

Preparation of Plasmid pUB110

Plasmid pUB110 (ATCC 37015) was isolated from *Bacillus subtilis* in accordance with the method described by Gryczan et al. in *Journal of Bacteriology*, Vol. 134, pp. 318–329 (1978).

EXAMPLE 2-(3)

Preparation of Recombinant DNA Carrying Polypeptide Gene

The recombinant DNA pTCH201 carrying the heat-resistant-polypeptide gene prepared in Example 2-(1), was completely digested by subjecting it simultaneously to restriction enzymes EcoRI and XbaI.

Separately, the plasmid pUB110 specimen, prepared in Example 2-(2), was completely cleaved by subjecting it to restriction enzymes EcoRI and XbaI in the same manner.

The resultant fragments were subjected to $T_4$ DNA ligase similarly as in Example 1-(3) to obtain a recombinant DNA.

EXAMPLE 2-(4)

Introduction of Recombinant DNA into *Bacillus subtilis*

In this Example, *Bacillus subtilis* 715A, a strain incapable of producing amylase, was used as the host. The microorganism was cultured with brain heart infusion medium at 28° C. for 5 hours, and the cell, centrifugally collected from the culture, was then prepared into protoplast suspension in accordance with the method described by Schaeffer et al. in *Proceedings of the National Academy of Sciences of the USA*, Vol. 73, pp. 2151–2155 (1976).

To the suspension was added the recombinant DNA, prepared in Example 2-(3), and the mixture was then treated in accordance with the method described by Sekiguchi et al. in *Agricultural and Biological Chemistry*, Vol. 46, pp. 1617–1621 (1982) to effect transformation, spread on HCP medium containing 250 μg/ml of kanamycin and 10 mg/ml of starch, and incubated at 28° C. for 72 hours to form colonies.

From these colonies, recombinant microorganisms in which the recombinant DNA carrying the heat-resistant-polypeptide gene had been introduced were selected by the method in Example 1-(4). One of these microorganisms and its recombinant DNA were named as "*Bacillus subtilis* TCU211 (FERM BP2-2112)" and "pTCU211", respectively.

Figure 2:
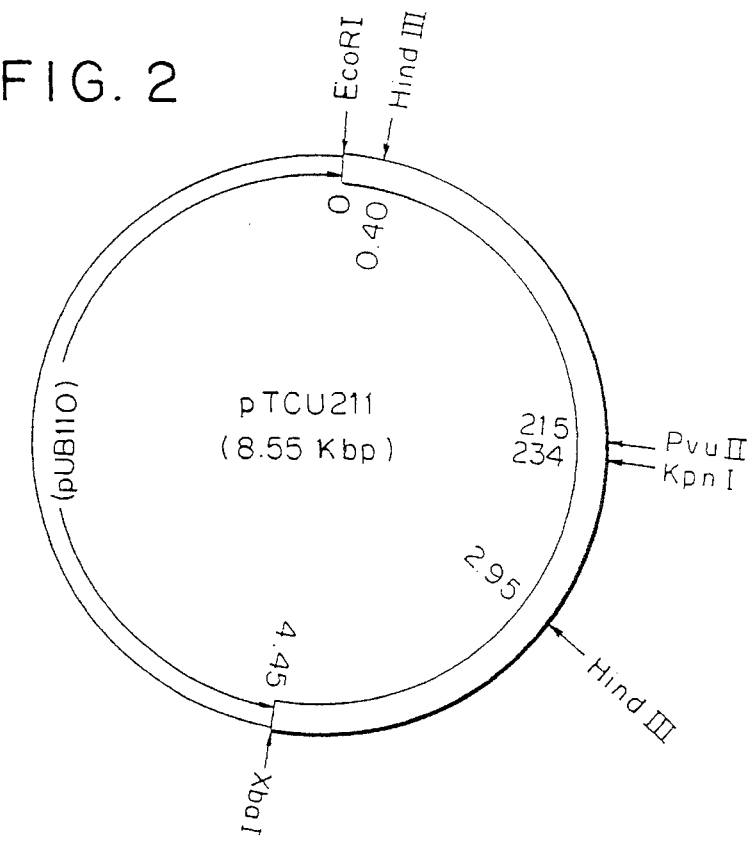
FIG. 2 shows the restriction map of recombinant DNA pTCU211, in particular that of the DNA fragment which carries the polypeptide gene derived from *Bacillus stearothermophilus*.

The restriction map of recombinant DNA pTCU211, in particular that of the DNA fragment derived from *Bacillus stearothermophilus* microorganism, is as shown in FIG. 2. FIG. 2 clearly shows that the DNA fragment carrying the polypeptide gene derived from *Bacillus stearothermophilus* microorganism is cleaved by either restriction enzyme PvuII, KpnI or HindIII, but not by EcoRI, BamHI, PstI, XhoI, BglII, AccI or XbaI.

EXAMPLE 3

N-terminal Amino Acid Sequence of *Bacillus stearothermophilus* Polypeptide

EXAMPLE 3-(1)

Preparation of Polypeptide

*Bacillus stearothermophilus* FERM-P No. 2225 was cultured with a liquid culture medium by the method in Example 5 to produce polypeptide. The supernatant, centrifugally obtained from the culture, was salted out with ammonium sulfate to obtain a polypeptide fraction which was then purified by column chromatography using "DEAE Toyopearl 650", an anion exchanger commercialized by Toyo Soda Manufacturing Co., Ltd., Tokyo, Japan, and chromatofocusing using "Mono P", a product of Pharmacia Fine Chemicals AB, Uppsala, Sweden, to obtain a highly-purified polypeptide specimen.

On SDS-polyacrylamide electrophoresis in accordance with the method described by K. Weber and M. Osborn in *Journal of Biological Chemistry*, Vol. 244, page 4406 (1969), the polypeptide specimen showed a molecular weight of 70,000±10,000 daltons.

The specific activity of the polypeptide specimen was 200±30 units/mg protein.

EXAMPLE 3-(2)

N-terminal Amino Acid Sequence of the Polypeptide

A polypeptide specimen, prepared by the method in Example 3-(1), was fed to "Model 470A", a gas-phase protein sequencer, a product of Applied Biosystems Inc., Calif., USA, and then analyzed with high-performance liquid chromatography to determine the N-terminal partial amino acid sequence.

The partial amino acid sequence was Ala-Gly-Asn-Leu-Asn-Lys-Val-Asn-Phe-Thr.

EXAMPLE 4

Sequence of Polypeptide Gene Derived from *Bacillus stearothermophilus* and Amino Acid Sequence of Polypeptide

EXAMPLE 4-(1)

Preparation of Plasmid pUC18

Plasmid pUC18 was prepared in accordance with the method in Example 1-(2) from *Escherichia coli* JM83 (ATCC 35607) in which the plasmid had been introduced.

EXAMPLE 4-(2)

Preparation of Recombinant DNA Carrying Polypeptide Gene

The recombinant DNA was prepared by the method in Example 1-(3).

A fragment, obtained by digesting a fragment carrying the polypeptide gene, prepared by the method in Example 2-(3), with restriction enzymes, and a plasmid fragment, obtained by cleaving a pUC18 specimen, prepared by the method in Example 4(1), in the same manner, were subjected to $T_4$ DNA ligase to obtain a recombinant DNA.

EXAMPLE 4-(3)

Introduction of Recombinant DNA into *Escherichia coli*

In this example, *Escherichia coli* JM83 was used as the host.

The recombinant DNA was introduced into this microorganism in accordance with the method in Example 1-(4) to transform the microorganism.

The recombinant microorganisms were inoculated to a culture medium containing 5-bromo-4-chloro-3-indoyl-β-galactoside (Xgal), and the microorganism forming colorless plaque was selected.

EXAMPLE 4-(4)

Preparation of Recombinant DNA from Recombinant Microorganism

The recombinant microorganism was cultured on L-broth containing 50 µg/ml of ampicillin, and the obtained cells were then treated with the alkaline mini-preparation method to obtain a recombinant DNA.

EXAMPLE 4-(5)

Sequence of Recombinant DNA

The recombinant DNA was sequenced by the dideoxy chain terminator method.

The recombinant DNA, prepared in Example 4-(4), and a synthetic primer composed of 17 bases were mixed, annealed at 60° C. for 20 minutes, mixed with dNTP, ddNTP, ($\alpha$-$^{32}$P) dCTP and Klenow fragment, and reacted at 37° C. for 30 minutes to extend the primer towards the 3' site from the 5' site. Thus, the complementary DNA was obtained. To the complementary DNA was added an excessive amount of dNTP, and the mixture was reacted at 37° C. for 30 minutes, followed by addition of a formamide solution of dye mixture to suspend the reaction. The reaction mixture was boiled for 3 minutes, and electrophoresed on 6% polyacrylamide gel at about 25 mA (about 2,000 volts) to separate the extended complementary DNA. After completion of the electrophoresis, the gel was fixed and dehydrated.

The dehydrated gel was then autographed, and the polypeptide gene was determined by analyzing the base bands on the radioauogram.

The results are as shown in FIG. 5.

The signal peptide gene located upstream of the 5'-terminal end of the polypeptide gene was sequenced in the same manner.

The results are as shown in FIG. 6.

EXAMPLE 4-(6)

Amino Acid Sequence of the Polypeptide

The amino acid sequence of the polypeptide was determined with reference to the sequence as shown in FIG. 5, and the results are as shown in FIG. 8.

The amino acid sequence of the signal peptide was determined in the same manner, and the results are as shown in FIG. 7.

This evidence confirms that the polypeptide derived from *Bacillus stearothermophilus* has the amino acid sequence as shown in FIG. 8.

EXAMPLE 5

Preparation of Polypeptide with Recombinant Microorganism

Polypeptides were prepared with recombinant microorganisms *Escherichia coli* TCH201 (FERMBP-2109) and *Bacillus subtilis* TCU211 (FERM BP-2112) both in which recombinant DNA carrying the heat-resistant-polypeptide gene derived from *Bacillus stearothermophilus* had been introduced.

The polypeptide productivities of these recombinant microorganisms were compared with those of the host microorganisms without the recombinant plasmid and the donor *Bacillus stearothermophilus* microorganism in relation to their CGTase activity. A liquid culture medium consisting of 1.0 w/v % corn steep liquor, 0.1 w/v % ammonium sulfate, 1.0 w/v % calcium carbonate, 1 w/v % starch and water was adjusted to pH 7.2, sterilized by heating at 120° C. for 20 minutes, and cooled. In the case of *Escherichia coli* TCH201, the liquid culture medium was mixed with 50 µg/ml of ampicillin and the microorganism was inoculated to the liquid culture medium. *Escherichia coli* HB101 was inoculated to the liquid culture medium without addition of antibiotic. In each case, the microorganism was cultured at 37° C. for 48 hours under vigorous shaking conditions.

Separately, *Bacillus subtilis* TCU211 was inoculated to the liquid culture medium additionally containing 5 µg/ml of kanamycin, while *Bacillus subtilis* 715A was inoculated to the liquid culture medium without addition of antibiotic. In each case, the microorganism was cultured at 28° C. for 72 hours.

*Bacillus stearothermophilus* FERM-P No. 2225 was cultured with the liquid culture medium at 50° C. for 48 hours without addition of antibiotic. After separation of each culture into supernatant and cells by centrifugation, the supernatant was assayed intact for CGTase activity, while the cells were ultrasonically broken, prior to determination of their CGTase activity per culture. The results are as shown in Table 1.

TABLE 1

| Microorganism | CGTase activity (units/ml) | | | |
|---|---|---|---|---|
| | Supernatant | Cell | Total | |
| *Escherichia coli* TCH201 (FERM BP-2109) | 0.8 | 13.5 | 14.3 | Present invention |
| *Bacillus subtilis* TCU211 (FERM BP-2110) | 46.7 | 20.5 | 67.2 | Present invention |
| *Escherichi coli* HB101 | 0 | 0 | 0 | Control |
| *Bacillus subtilis* 715A | 0 | 0 | 0 | Control |
| *Bacillus stearothermophilus* FERM-P No. 2225 | 8.5 | 0.3 | 8.8 | Control |

This evidence clearly shows that the recombinant microorganisms are advantageously usable in industrial-scale production of polypeptide because these microorganisms possess an improved polypeptide productivity.

The supernatants were salted out with ammonium sulfate at a saturation degree of 0.6 to obtain crude polypeptide specimens. After studying these polypeptide specimens on their enzymatic properties, such as saccharide transfer from starch to sucrose, cyclodextrin production from starch, ratio of $\alpha$-, $\beta$- and $\gamma$-cyclodextrins, optimum temperature, optimum pH, stable temperature range and stable pH range, the properties of the polypeptide produced by the recombinant microorganism were in good accordance with those of the polypeptide produced by the donor *Bacillus stearothermophilus* microorganism.

EXAMPLE 6

Cloning of *Bacillus macerans* Polypeptide Gene into *Escherichia coli*

EXAMPLE 6-(1)

Preparation of Chromosome DNA Carrying *Bacillus macerans* Polypeptide Gene

The polypeptide gene was prepared in accordance with the method in Example 1-(1), except that *Bacillus macetans* 17A was cultured at 28° C.

EXAMPLE 6-(2)

Preparation of Recombinant DNA Carrying Polypeptide Gene

The chromosomal DNA carrying the polypeptide gene derived from *Bacillus macerans*, prepared in Example 6-(1), was partially digested similarly as in Example 1-(3) with restriction enzyme HindIII, purchased from Nippon Gene Co., Ltd.

Separately, a plasmid pBR322 specimen, prepared by the method in Example 1-(2), was completely cleaved with restriction enzyme HindIII, and the 5'-terminal end of the cleaved product was dephosphorized by the method in Example 1-(3). The fragments thus obtained were ligated in accordance with the method in Example-(3) to obtain a recombinant DNA.

EXAMPLE 6-(3)

Introduction of Recombinant DNA into *Escherichia coli*

The recombinant microorganism in which recombinant DNA had been introduced was cloned in accordance with the method in Example 1-(4) using *Escherichia coli* HB101 (ATCC 33694), a strain incapable of producing amylase, as the host. Thereafter, the recombinant DNA was isolated from the microorganism, subjected to restriction enzymes to determine the restriction cleavage sites, and partially digested with restriction enzyme Sau3AI commercialized by Nippon Gene Co., Ltd.

Separately, a plasmid pBR322 specimen, obtained by the method in Example 1-(2), was completely cleaved with restriction enzyme BamHI, and the 5'-terminal end of the resultant product was dephosphorized similarly as in Example 1-(3). The obtained fragments were ligated with $T_4$ DNA ligase to obtain a recombinant DNA, followed by selecting recombinant microorganisms in accordance with the method in Example 1-(4). The recombinant microorganisms contained a recombinant DNA of a relatively small-size that carries the polypeptide gene.

One of these recombinant microorganisms and its recombinant DNA were named as "*Escherichia coli* MAH2 (FERM BP-2110)" and "pMAH2" respectively.

Figure 3:
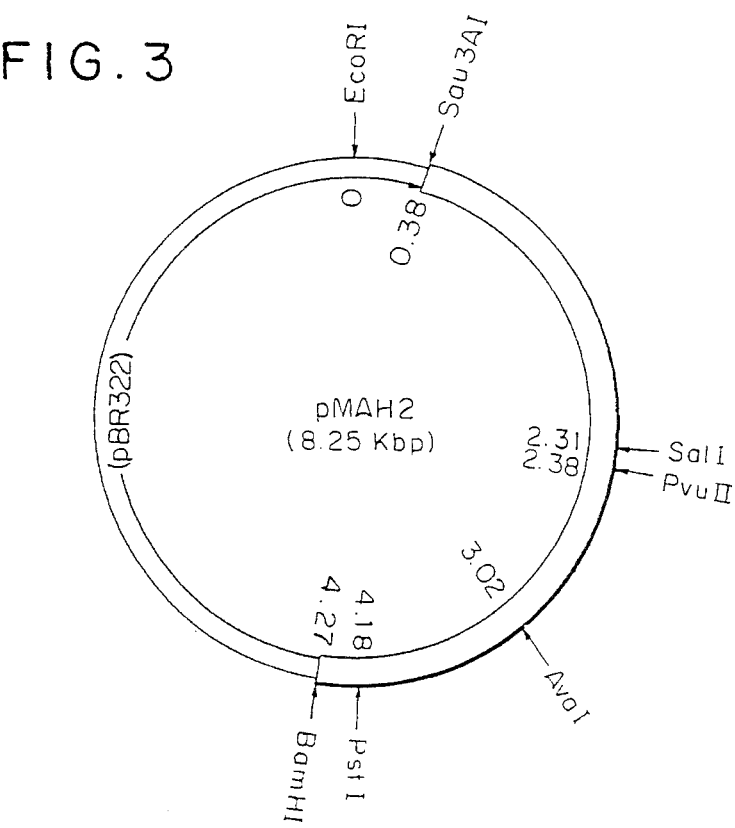
FIG. 3 shows the restriction map of recombinant DNA pMAH2, in particular that of the DNA fragment which carries the polypeptide gene derived from *Bacillus macerans*.

The restriction map of recombinant DNA pMAH2, in particular that of the DNA fragment that carries the polypeptide gene derived from *Bacillus macerans*, is as shown in FIG. 3.

FIG. 3 shows that the DNA fragment carrying the polypeptide gene derived from *Bacillus macerans* is cleaved by either restriction enzyme PvuII, SalI, AvaI commercialized by Nippon Gene Co., Ltd., or PstI commercialized by Nippon Gene Co., Ltd., but not by EcoRI, HindIII, KpnI, BamHI, XbaI, XhoI or Sma.

EXAMPLE 7

Cloning of *Bacillus macerans* Polypeptide Gene into *Bacillus subtilis*

EXAMPLE 7-(1)

Preparation of Recombinant DNA pMAH2

The recombinant DNA pMAH2 was isolated from *Escherichia coli* MAH2 (FERM BP-2110) in accordance with the method in Example 1-(2).

EXAMPLE 7-(2)

Preparation of Recombinant DNA Carrying the Polypeptide Gene

The recombinant DNA pMAH2 specimen carrying the polypeptide gene, prepared in Example 7-(1), was completely digested by subjecting it simultaneously to restriction enzymes EcoRI and BamHI.

The fragments thus obtained were subjected to $T_4$ DNA ligase similarly as in Example 1-(3) to obtain a recombinant DNA.

EXAMPLE 7-(3)

Introduction of Recombinant DNA into *Bacillus subtilis*

Recombinant microorganisms in which recombinant DNA carrying the polypeptide gene derived from *Bacillus macerans* had been introduced were cloned in accordance with the method in Example 2-(4) using *Bacillus subtilis* 715A, a strain incapable of producing amylase.

Figure 4:
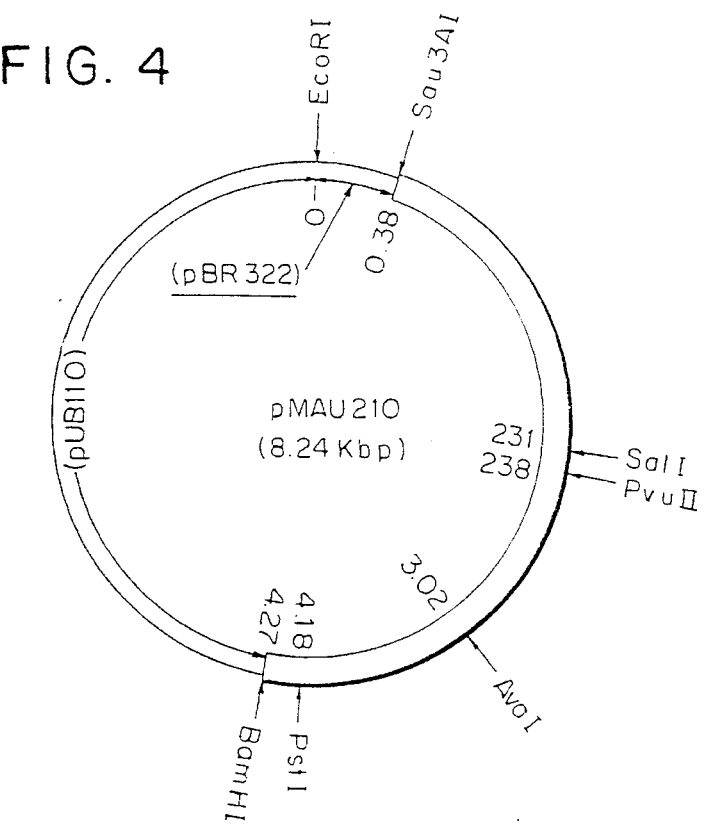
FIG. 4 shows the restriction map of recombinant DNA pMAU210, in particular that of the DNA fragment which carries the polypeptide gene derived from *Bacillus macetans*.

One of the recombinant microorganisms and its recombinant DNA were named as "*Bacillus subtilis* MAU210 (FERM BP-2111)" and "pMAU210" respectively. The restriction map of recombinant DNA pMAU210, in particular that of the DNA fragment that carries the polypeptide gene derived from *Bacillus macerans*, was as shown in FIG. 4. FIG. 4 shows that this DNA fragment carrying the polypeptide gene derived from *Bacillus macerans* is cleaved by either restriction enzyme PvuII, SalI, AvaI or PstI, but not by EcoRI, HindIII, KpnI, BamHi, XbaI, XhoI or SmaI. cl EXAMPLE 8

N-terminal Amino Acid Sequence of the Polypeptide Derived From *Bacillus macetans*

EXAMPLE 8-(1)

Preparation of Polypeptide

The polypeptide was produced by culturing *Bacillus subtilis* MAU210 (FERM BP-2111) with a liquid culture medium similarly as in Example 10 and then purifying in accordance with the method in Example 4-(1) to obtain a high-purity polypeptide specimen.

On SDS-polyacrylamide electrophoresis, the polypeptide specimen showed a molecular weight of 70,000±10,000 daltons and a specific activity of 200±30 units/mg protein.

EXAMPLE 8-(2)

N-terminal Amino Acid Sequence

The partial amino acid sequence containing the N-terminal end was determined with the polypeptide specimen prepared in Example 8-(1), in accordance with the method in Example 3-(2).

The partial amino acid sequence was Ser-Pro-Asp-Thr-Ser-Val-Asn-Asn-Lys-Leu.

EXAMPLE 9

Sequence of Polypeptide Gene Derived from *Bacillus macerans* and Amino Acid Sequence of Polypeptide

EXAMPLE 9-(1)

Preparation of Recombinant DNA Carrying the Polypeptide Gene

The recombinant DNA was prepared in accordance with the method in Example 4-(3).

More particularly, a DNA fragment, obtained by digesting a DNA fragment carrying the polypeptide gene, prepared by the method in Example 7-(2), with restriction enzymes, and a plasmid fragment, obtained by cleaving a plasmid pUC18 specimen, prepared by the method in Example 4-(2), in the same manner, were ligated with $T_4$ DNA ligase to obtain a recombinant DNA.

EXAMPLE 9-(2)

Introduction of Recombinant DNA into *Escherichia coli*

The recombinant DNA was introduced in accordance with the method in Example 4-(3) into *Escherichia coli* JM83 as the host microorganism to obtain a recombinant microorganism.

EXAMPLE 9-(3)

Preparation of Recombinant DNA from Recombinant Microorganism

The recombinant DNA was prepared in accordance with the method in Example 4-(4).

EXAMPLE 9-(4)

Sequence of Recombinant DNA

The polypeptide gene was sequenced in accordance with the method in Example 4-(5).

The results are as shown in FIG. 9.

The signal peptide located upstream of the 5'-site of the polypeptide gene was sequenced in the same manner.

The results are as shown in FIG. 10.

EXAMPLE 9-(5)

Amino Acid Sequence of Polypeptide

The amino acid sequence of the polypeptide was determined with reference to the sequence of one polypeptide gene. The results are as shown in FIG. 12.

The amino acid sequence of the signal peptide was determined in the same manner. The results are as shown in FIG. 11.

This evidence confirms that the polypeptide derived from *Bacillus macetans* has the amino acid sequence as shown in FIG. 12.

The evidence as shown in FIGS. 8 and 12 show that each polypeptide has the following common amino acid sequences:

(a) Asn-Lys-Ile-Asn-Asp-Gly-Tyr-Leu-Thr, (b) Pro-Val-Phe-Thr-Phe-Gly-Glu-Trp-Phe-Leu, (c) Val-Thr-Phe-Ile-Asp-Asn-His-Asp-Met-Asp-Arg-Phe, (d) Ile-Tyr-Tyr-Gly-Thr-Glu-Gln-Tyr-Met-Thr-Gly-Asn-Gly-Asp-Pro-Asn-Asn-Arg, and (e) Asn-Pro-Ala-Leu-Ala-Tyr-Gly, as well as that these partial amino acid sequences (a), (b), (c), (d) and (e) are located in order of nearness to the N-terminal end of the polypeptide. These common sequences are underlined in FIGS. 8 and 12.

EXAMPLE 10

Preparation of Polypeptide with Recombinant Microorganism

Polypeptides were prepared with *Escherichia coli* MAH2 (FERM BP-2110) and *Bacillus subtilis* MAU210 (FERM BP-2111) both in which recombinant DNA carrying the polypeptide gene derived from *Bacillus macerans* had been introduced. The polypeptide productivities of these recombinant microorganisms, the host microorganisms without addition of the recombinant plasmid, and the donor *Bacillus macetans* microorganism were compared in relation to their CGTase activity. A liquid culture medium prepared by the method in Example 5 was used.

*Escherichia coli* MAH2 was inoculated to the liquid culture medium additionally containing 50 µg/ml of ampicillin, while *Escherichia coli* HB101 was inoculated to the liquid culture medium without addition of antibiotic. In each case, the microorganism was cultured at 35° C. for 24 hours under vigorous shaking conditions.

*Bacillus subtilis* MAU210 was inoculated to the liquid culture medium additionally containing 5 µg/ml of kanamycin, while *Bacillus subtilis* 715A was inoculated to the liquid culture medium without addition of antibiotic. In each case, microorganism was cultured at 28° C. for 72 hours.

*Bacillus macerans* 17A was cultured with the liquid culture medium at 28° C. for 72 hours without addition of antibiotic.

Each culture was treated similarly as in Example 5, and its CTGase activity was then determined. The results are as shown in Table 2.

TABLE 2

| Microorganism | CGTase activity (units/ml) | | | |
|---|---|---|---|---|
| | Super-natant | Cell | Total | |
| *Escherichia coli* MAH2 (FERM P-7925) | 0.6 | 11.8 | 12.4 | Present invention |
| *Bacillus subtilis* MAU210 (FERM P-7926) | 54.6 | 0.3 | 54.9 | Present invention |
| *Escherichi coli* HB101 | 0 | 0 | 0 | Control |
| *Bacillus subtilis* 715A | 0 | 0 | 0 | Control |
| *Bacillus macerans* 17A | 7.5 | 0.4 | 7.9 | Control |

This evidence clearly shows that the recombinant microorganisms are advantageously usable in industrial-scale production of polypeptide because they have an improved polypeptide productivity.

The supernatants were salted out with ammonium sulfate at a saturation degree of 0.6 to obtain crude polypeptide specimens.

On studying these crude polypeptide specimens on their enzymatic properties similarly as in Example 5, the enzymatic properties of the polypeptide produced by the recombinant microorganisms were in good accordance with those of the polypeptide produced by the donor *Bacillus macetans* microorganism.

Principal uses of the polypeptide will hereinafter be described.

The polypeptide effects the intra- or intermolecular saccharide transfer reaction between suitable saccharide donor and saccharide acceptor.

According to one aspect of the present invention, various saccharide-transferred products can be produced by taking advantage of these saccharide transfer reactions.

For example, a partial starch hydrolysate containing α-, β- and γ-cyclodextrins is prepared by subjecting an amylaceous substance as the substrate, such as starch, liquefied starch with a Dextrose Equivalent (DE) of below 10, or amylose, to the action of the polypeptide utilizing the intramolecular saccharide transfer reaction. Each cyclodextrin can be isolated from the partial starch hydrolysate, if necessary.

α-Glycosylated saccharide sweetener, for example, α-glycosyl-, α-maltosyl- and α-maltotriosyl-saccharides, is prepared by subjecting a mixture of a saccharide donor, for example, amylaceous substance such as starch, liquefied starch, dextrin, cyclodextrin or amylose; and a saccharide acceptor, for example, monosaccharide such as xylose, sorbose or fructose, or disaccharide such as sucrose, maltulose or isomaltulose, to the action of polypeptide utilizing the intermolecular saccharide transfer action. The α-glycosylated saccharine sweetener can be advantageously used in foods and beverages because the α-glycosylated saccharide sweetener is much milder in taste, more soluble in water, but less crystallizable in comparison with intact saccharide sweetener. These would expand extremely the use of saccharide sweeteners.

In the intermolecular saccharide transfer reaction, the use of a glycoside, for example, steviol glycoside such as stevioside or rebaudioside, glycyrrhizin, soyasaponin, teasaponin, rutin or esculin, as the saccharide acceptor leads to the formation of α-glycosylated glycosides such as α-glucosyl-, α-maltosyl- and α-maltotriosyl-glycosides. The α-glycosylated glycoside is free of the unpleasant tastes such as bitter- and astringent-tastes which are inherent to intact glycoside, and more readily soluble in water than intact glycoside. These would expand extremely the use of glycosides. Specifically, α-glycosylated steviol glycoside and α-glycosylated glycyrrhizin can be advantageously used in foods, beverages, and pharmaceuticals for peroral administration because the taste improvement in these α-glycosylated glycosides is remarkably high, as well as because their sweetness is comparable to that of sucrose.

Several embodiments will be disclosed.

EXAMPLE 11

Corn Syrup Containing Cyclodextrin

A 10 w/w % suspension of potato starch was mixed with 2 units/g starch of a polypeptide specimen prepared with *Bacillus subtilis* TCU211 in accordance with the method in Example 5, liquefied by heating to 85° C. at pH 6.5, cooled to 70° C., further mixed with the same amount of the polypeptide specimen, and reacted for 40 hours. The reaction mixture was purified by decoloration using activated carbon and deionization using ion exchange resin, and then concentrated to obtain a starch syrup containing cyclodextrin in a yield of 92% based on the dry solid. The corn syrup can be advantageously incorporated into flavors and cosmetics wherein fragrance or aroma is one of the important factors because the corn syrup is excellent in flavor-locking properties.

The α-, β- and γ-cyclodextrins in the corn syrup can be separated by treating it with a procedure using organic precipitant, such as toluene or trichloromethane, or conventional column chromatography.

EXAMPLE 12

α-Glycosylsucrose

A 35 w/w % suspension of cornstarch was mixed with 0.2 w/w % oxalic acid, autoclaved to 120° C. to give a DE of 20, neutralized with calcium carbonate, and filtered to obtain a dextrin solution. The dextrin solution was then mixed with a half amount of sucrose based on the dry solid, and the resultant mixture was mixed with 15 units/g starch of a polypeptide specimen prepared with *Bacillus subtilis* MAU210 in accordance with the method in Example 10, and reacted at pH 6.0 and 55° C. for 40 hours. The reaction mixture was purified by decoloration using activated carbon and deionization using ion exchange resin, and then concentrated to obtain a colorless, transparent corn syrup in a yield of 94% based on the dry solid. The corn syrup containing a large amount of α-glycosylsucrose can be advantageously used in confectioneries because it is mildly sweet and amorphous.

EXAMPLE 13

α-Glycosyl Stevioside

Two-hundred g of stevioside and 600 g of dextrin (DE 8) were dissolved in 3 liters of water by heating, and the resultant solution was cooled to 70° C., mixed with 5 units/g dextrin of a polypeptide specimen prepared with *Bacillus subtilis* TCU211 in accordance with the method in Example 5, and reacted at pH 6.0 and 65° C. for 35 hours. The reaction mixture was then heated to 95° C. for 15 minutes, purified by filtration, concentrated, and pulverized to obtain a pulverulent sweetener containing α-glycosyl stevioside in a yield of about 92% based on the dry solid.

The sweetener, free of the unpleasant taste which is inherent to intact stevioside, was comparable to sucrose in taste quality, and the sweetening power of the sweetener was about 100-fold higher than that of sucrose. The sweetener can be advantageously used as a diet sweetener or to season foods and beverages because of its low-cariogenic and low-calorific properties.

EXAMPLE 14

α-Glycosyl Ginsenoside

Sixty g of a ginseng extract and 180 g of β-cyclodextrin were dissolved in 500 ml of water by heating, and the resultant mixture was cooled to 70° C., adjusted to pH 6.0, mixed with 3 units/g β-cyclodextrin of a polypeptide specimen prepared with *Escherichia coli* TCH201 in accordance with the method in Example 5, cooled to 65° C., and reacted to pH 6.0 for 40 hours. The reaction mixture was heated for 15 minutes to inactivate the polypeptide, followed by filtration. The filtrate was admitted to a column packed with 3 liters of "Amberlite XAD-7", a synthetic adsorbent commercialized by Rohm & Haas Co., Philadelphia, Pa., USA; thereafter, the column was sufficiently washed with water remove free saccharides. To the column was then admitted 10 to liters of 50 v/v % ethanol, and the eluate was concentrated and dehydrated to obtain about 21 g of a pulverulent product that contains α-glycosyl ginsenoside. Since the product is free of the unpleasant tastes such as bitter-, astringent- and harsh-tastes which are inherent to intact ginsenoside, the product can be perorally administered intact, or, if necessary, seasoned with any sweetener or sour, prior to its use. In addition, the product can be advantageously used in health foods and medicines for internal administration because the product possesses invigorating, peptic, intestine-regulating, haematic, anti-inflammatory and expectorant effects as intact ginsenoside does.

As described above, the present inventors determined the sequences of the CGTase polypeptide gene and its signal peptide, and prepared the recombinant DNA having a PvuII restriction site from a donor microorganism by in vitro genetic engineering techniques. Furthermore, the present inventors prepared recombinant microorganisms in which the recombinant DNA is introduced, as well as confirming that the recombinant microorganisms autonomically and consistently proliferate in a nutrient culture medium.

In view of adequately supplying polypeptide, the present invention is industrially significant because the present invention assures a wide polypeptide source and easily improves the polypeptide productivity of donor microorganisms.

While there has been described what is at present considered to be the preferred embodiments of the invention, it will be understood that various modifications may be made therein, and it is intended to cover in the appended claims all such modifications as fall within the true spirit and scope of the invention.

What is claimed is:

1. A process for producing a saccharide-transferred product, comprising the steps of:

introducing a recombinant DNA carrying isolated promoter and structural gene sequences coding for the expression of a polypeptide possessing cyclomaltodextrin glucanotransferase (CGTase) activity and comprising one or more partial amino acid sequences selected from the group consisting of:

(a) Asn-Lys-Ile-Asn-Asp-Gly-Tyr-Leu-Thr, (b) Pro-Val-Phe-Thr-Phe-Gly-Glu-Trp-Phe-Leu, (c) Val-Thr-Phe-Ile-Asp-Asn-His-Asp-Met-Asp-Arg-Phe, (d) Ile-Tyr-Tyr-Gly-Thr-Glu-Gln-Tyr-Met-Thr-Gly-Asn-Gly-Asp-Pro-Asn-Asn-Arg, and (e) Asn-Pro-Ala-Leu-Ala-Tyr-Gly, into a host microorganism to obtain a recombinant microorganism;

culturing with a nutrient culture medium said recombinant microorganism having said recombinant DNA for the expression of said polypeptide;

recovering the accumulated polypeptide; and subjecting an amylaceous substance to the action of said recovered polypeptide possessing cyclomaltodextrin glucanotransferase activity to produce a saccharide-transferred product.

2. The process in accordance with claim 1, wherein said saccharide-transferred product is cyclodextrin.

3. The process in accordance with claim 1, wherein said amylaceous substance is subjected to the action of said polypeptide in the presence of a saccharide acceptor.

4. The process in accordance with claim 1, wherein said amylaceous substance is selected from the group consisting of starch, amylose, cyclodextrin, dextrin, and mixtures thereof.

5. The process in accordance with claim 3, wherein said saccharide acceptor is a member selected from the group consisting of saccharide sweetener, glycoside, and mixtures thereof.

6. The process in accordance with claim 3, wherein the saccharide-transferred product is a member selected from the group consisting of α-glycosytsucrose, α-glycosyl stevioside, and α-glycosyl ginsenoside.

7. The process in accordance with claim 3, wherein said saccharide-transferred product is used as a sweetener.

8. The process in accordance with claim 1, wherein said host microorganism is of the genus Escherichia or Bacillus.

9. The process in accordance with claim 1, wherein said recombinant microorganism is a member selected from the group consisting of Escherichia coli TCH201 (FERM BP-2109) or Escherichia coli MAH2 (FERM BP-2110).

10. The process in accordance with claim 1, wherein said recombinant microorganism is a member selected from the group consisting of Bacillus subtilis MAU210 (FERM BP-2111) and Bacillus subtilis TCU211 (FERM BP-2112).

11. The process in accordance with claim 1, wherein said polypeptide possessing cyclomaltodextrin glucanotransferase activity has the following amino acid sequence:

|      | 1   | 2   | 3   | 4   | 5   | 6   | 7   | 8   | 9   | 10  | 11  | 12  | 13  | 14  | 15  |
|------|-----|-----|-----|-----|-----|-----|-----|-----|-----|-----|-----|-----|-----|-----|-----|
| 1>   | Ala | Gly | Asn | Leu | Asn | Lys | Val | Asn | Phe | Thr | Ser | Asp | Val | Val | Tyr |
| 16>  | Gln | Ile | Val | Val | Asp | Arg | Phe | Val | Asp | Gly | Asn | Thr | Ser | Asn | Asn |
| 31>  | Pro | Ser | Gly | Ala | Leu | Phe | Ser | Ser | Gly | Cys | Thr | Asn | Leu | Arg | Lys |
| 46>  | Tyr | Cys | Gly | Gly | Asp | Trp | Gln | Gly | Ile | Ile | Asn | Lys | Ile | Asn | Asp |
| 61>  | Gly | Tyr | Leu | Thr | Asp | Met | Gly | Val | Thr | Ala | Ile | Trp | Ile | Ser | Gln |
| 76>  | Pro | Val | Glu | Asn | Val | Phe | Ser | Val | Met | Asn | Asp | Ala | Ser | Gly | Ser |
| 91>  | Ala | Ser | Tyr | His | Gly | Tyr | Trp | Ala | Arg | Asp | Phe | Lys | Lys | Pro | Asn |
| 106> | Pro | Phe | Phe | Gly | Thr | Leu | Ser | Asp | Phe | Gln | Arg | Leu | Val | Asp | Ala |
| 121> | Ala | His | Ala | Lys | Gly | Ile | Lys | Val | Ile | Ile | Asp | Phe | Ala | Pro | Asn |
| 136> | His | Thr | Ser | Pro | Ala | Ser | Glu | Thr | Asn | Pro | Ser | Tyr | Met | Glu | Asn |
| 151> | Gly | Arg | Leu | Tyr | Asp | Asn | Gly | Thr | Leu | Leu | Gly | Gly | Tyr | Thr | Asn |
| 166> | Asp | Ala | Asn | Met | Tyr | Phe | His | His | Asn | Gly | Gly | Thr | Thr | Phe | Ser |
| 181> | Ser | Leu | Glu | Asp | Gly | Ile | Tyr | Arg | Asn | Leu | Phe | Asp | Leu | Ala | Asp |
| 196> | Leu | Asn | His | Gln | Asn | Pro | Val | Ile | Asp | Arg | Tyr | Leu | Lys | Asp | Ala |
| 211> | Val | Lys | Met | Trp | Ile | Asp | Met | Gly | Ile | Asp | Gly | Ile | Arg | Met | Asp |
| 226> | Ala | Val | Lys | His | Met | Pro | Phe | Gly | Trp | Gln | Lys | Ser | Leu | Met | Asp |
| 241> | Glu | Ile | Asp | Asn | Tyr | Arg | Pro | Val | Phe | Thr | Phe | Gly | Glu | Trp | Phe |
| 256> | Leu | Ser | Glu | Asn | Glu | Val | Asp | Ala | Asn | Asn | His | Tyr | Phe | Ala | Asn |
| 271> | Glu | Ser | Gly | Met | Ser | Leu | Leu | Asp | Phe | Arg | Phe | Gly | Gln | Lys | Leu |
| 286> | Arg | Gln | Val | Leu | Arg | Asn | Asn | Ser | Asp | Asn | Trp | Tyr | Gly | Phe | Asn |
| 301> | Gln | Met | Ile | Gln | Asp | Thr | Ala | Ser | Ala | Tyr | Asp | Glu | Val | Leu | Asp |
| 316> | Gln | Val | Thr | Phe | Ile | Asp | Asn | His | Asp | Met | Asp | Arg | Phe | Met | Ile |
| 331> | Asp | Gly | Gly | Asp | Pro | Arg | Lys | Val | Asp | Met | Ala | Leu | Ala | Val | Leu |
| 346> | Leu | Thr | Ser | Arg | Gly | Val | Pro | Asn | Ile | Tyr | Tyr | Gly | Thr | Glu | Gln |
| 361> | Tyr | Met | Thr | Gly | Asn | Gly | Asp | Pro | Asn | Asn | Arg | Lys | Met | Met | Ser |
| 376> | Ser | Phe | Asn | Lys | Asn | Thr | Arg | Ala | Tyr | Gln | Val | Ile | Gln | Lys | Leu |
| 391> | Ser | Ser | Leu | Arg | Arg | Asn | Asn | Pro | Ala | Leu | Ala | Tyr | Gly | Asp | Thr |

|      | 1   | 2   | 3   | 4   | 5   | 6   | 7   | 8   | 9   | 10  | 11  | 12  | 13  | 14  | 15  |
| ---- | --- | --- | --- | --- | --- | --- | --- | --- | --- | --- | --- | --- | --- | --- | --- |
| 406> | Glu | Gln | Arg | Trp | Ile | Asn | Gly | Asp | Val | Tyr | Val | Tyr | Glu | Arg | Gln |
| 421> | Phe | Gly | Lys | Asp | Val | Val | Leu | Val | Arg | Val | Asn | Arg | Ser | Ser | Ser |
| 436> | Ser | Asn | Tyr | Ser | Ile | Thr | Gly | Leu | Phe | Thr | Ala | Leu | Pro | Ala | Gly |
| 451> | Thr | Tyr | Thr | Asp | Gln | Leu | Gly | Gly | Leu | Leu | Asp | Gly | Asn | Thr | Ile |
| 466> | Gln | Val | Gly | Ser | Asn | Gly | Ser | Val | Asn | Ala | Phe | Asp | Leu | Gly | Pro |
| 481> | Gly | Glu | Val | Gly | Val | Trp | Ala | Tyr | Ser | Ala | Thr | Glu | Ser | Thr | Pro |
| 496> | Ile | Ile | Gly | His | Val | Gly | Pro | Met | Met | Gly | Gln | Val | Gly | His | Gln |
| 511> | Val | Thr | Ile | Asp | Gly | Glu | Gly | Phe | Gly | Thr | Asn | Thr | Gly | Thr | Val |
| 526> | Lys | Phe | Gly | Thr | Thr | Ala | Ala | Asn | Val | Val | Ser | Trp | Ser | Asn | Asn |
| 541> | Gln | Ile | Val | Val | Ala | Val | Pro | Asn | Val | Ser | Pro | Gly | Lys | Tyr | Asn |
| 556> | Ile | Thr | Val | Gln | Ser | Ser | Ser | Gly | Gln | Thr | Ser | Ala | Ala | Tyr | Asp |
| 571> | Asn | Phe | Glu | Val | Leu | Thr | Asn | Asp | Gln | Val | Ser | Val | Arg | Phe | Val |
| 586> | Val | Asn | Asn | Ala | Thr | Thr | Asn | Leu | Gly | Gln | Asn | Ile | Tyr | Ile | Val |
| 601> | Gly | Asn | Val | Tyr | Glu | Leu | Gly | Asn | Trp | Asp | Thr | Ser | Lys | Ala | Ile |
| 616> | Gly | Pro | Met | Phe | Asn | Gln | Val | Val | Tyr | Ser | Tyr | Pro | Thr | Trp | Tyr |
| 631> | Ile | Asp | Val | Ser | Val | Pro | Glu | Gly | Lys | Thr | Ile | Glu | Phe | Lys | Phe |
| 646> | Ile | Lys | Lys | Asp | Ser | Gln | Gly | Asn | Val | Thr | Trp | Glu | Ser | Gly | Ser |
| 661> | Asn | His | Val | Tyr | Thr | Thr | Pro | Thr | Asn | Thr | Thr | Gly | Lys | Ile | Ile |
| 676> | Val | Asp | Trp | Gln | Asn |     |     |     |     |     |     |     |     |     |     |

12. The process in accordance with claim 1, wherein said polypeptide possessing cyclomaltodextrin glucanotransferase activity has the following amino acid sequence:

|      | 1   | 2   | 3   | 4   | 5   | 6   | 7   | 8   | 9   | 10  | 11  | 12  | 13  | 14  | 15  |
| ---- | --- | --- | --- | --- | --- | --- | --- | --- | --- | --- | --- | --- | --- | --- | --- |
| 1>   | Ser | Pro | Asp | Thr | Ser | Val | Asn | Asn | Lys | Leu | Asn | Phe | Ser | Thr | Asp |
| 16>  | Thr | Val | Tyr | Gln | Ile | Val | Thr | Asp | Arg | Phe | Val | Asp | Gly | Asn | Ser |
| 31>  | Ala | Asn | Asn | Pro | Thr | Gly | Ala | Ala | Phe | Ser | Ser | Asp | His | Ser | Asn |
| 46>  | Leu | Lys | Leu | Tyr | Phe | Gly | Gly | Asp | Trp | Gln | Gly | Ile | Thr | Asn | Lys |
| 61>  | Ile | Asn | Asp | Gly | Tyr | Leu | Thr | Gly | Met | Gly | Ile | Thr | Ala | Leu | Trp |
| 76>  | Ile | Ser | Gln | Pro | Val | Glu | Asn | Ile | Thr | Ala | Val | Ile | Asn | Tyr | Ser |
| 91>  | Gly | Val | Asn | Asn | Thr | Ala | Tyr | His | Gly | Tyr | Trp | Pro | Arg | Asp | Phe |
| 106> | Lys | Lys | Thr | Asn | Ala | Ala | Phe | Gly | Ser | Phe | Thr | Asp | Phe | Ser | Asn |
| 121> | Leu | Ile | Ala | Ala | Ala | His | Ser | His | Asn | Ile | Lys | Val | Val | Met | Asp |
| 136> | Phe | Ala | Pro | Asn | His | Thr | Asn | Pro | Ala | Ser | Ser | Thr | Asp | Pro | Ser |
| 151> | Phe | Ala | Glu | Asn | Gly | Ala | Leu | Tyr | Asn | Asn | Gly | Thr | Leu | Leu | Gly |
| 166> | Lys | Tyr | Ser | Asn | Asp | Thr | Ala | Gly | Leu | Phe | His | His | Asn | Gly | Gly |
| 181> | Thr | Asp | Phe | Ser | Thr | Thr | Glu | Ser | Gly | Ile | Tyr | Lys | Asn | Leu | Tyr |
| 196> | Asp | Leu | Ala | Asp | Ile | Asn | Gln | Asn | Asn | Asn | Thr | Ile | Asp | Ser | Tyr |
| 211> | Leu | Lys | Glu | Ser | Ile | Gln | Leu | Trp | Leu | Asn | Leu | Gly | Val | Asp | Gly |
| 226> | Ile | Arg | Phe | Asp | Ala | Val | Lys | His | Met | Pro | Gln | Gly | Trp | Gln | Lys |
| 241> | Ser | Tyr | Val | Ser | Ser | Ile | Tyr | Ser | Ser | Ala | Asn | Pro | Val | Phe | Thr |
| 256> | Phe | Gly | Glu | Trp | Phe | Leu | Gly | Pro | Asp | Glu | Met | Thr | Gln | Asp | Asn |
| 271> | Ile | Asn | Phe | Ala | Asn | Gln | Ser | Gly | Met | His | Leu | Leu | Asp | Phe | Ala |
| 286> | Phe | Ala | Gln | Glu | Ile | Arg | Glu | Val | Phe | Arg | Asp | Lys | Ser | Glu | Thr |
| 301> | Met | Thr | Asp | Leu | Asn | Ser | Val | Ile | Ser | Ser | Thr | Gly | Ser | Ser | Tyr |
| 316> | Asn | Tyr | Ile | Asn | Asn | Met | Val | Thr | Phe | Ile | Asp | Asn | His | Asp | Met |
| 331> | Asp | Arg | Phe | Gln | Gln | Ala | Gly | Ala | Ser | Thr | Arg | Pro | Thr | Glu | Gln |
| 346> | Ala | Leu | Ala | Val | Thr | Leu | Thr | Ser | Arg | Gly | Val | Pro | Ala | Ile | Tyr |
| 361> | Tyr | Gly | Thr | Glu | Gln | Tyr | Met | Thr | Gly | Asn | Gly | Asp | Pro | Asn | Asn |
| 376> | Arg | Gly | Met | Met | Thr | Gly | Phe | Asp | Thr | Asn | Lys | Thr | Ala | Tyr | Lys |
| 391> | Val | Ile | Lys | Ala | Leu | Ala | Pro | Leu | Arg | Lys | Ser | Asn | Pro | Ala | Leu |
| 406> | Ala | Tyr | Gly | Ser | Thr | Thr | Gln | Arg | Trp | Val | Asn | Ser | Asp | Val | Tyr |
| 421> | Val | Tyr | Glu | Arg | Lys | Phe | Gly | Ser | Asn | Val | Ala | Val | Val | Ala | Val |
| 436> | Asn | Arg | Ser | Ser | Thr | Thr | Ala | Tyr | Pro | Ile | Ser | Gly | Ala | Leu | Thr |
| 451> | Ala | Leu | Pro | Asn | Gly | Thr | Tyr | Thr | Asp | Val | Leu | Gly | Gly | Leu | Leu |
| 466> | Asn | Gly | Asn | Ser | Ile | Thr | Val | Asn | Gly | Gly | Thr | Val | Ser | Asn | Phe |
| 481> | Thr | Leu | Ala | Ala | Gly | Gly | Thr | Ala | Val | Trp | Gln | Tyr | Thr | Thr | Thr |
| 496> | Glu | Ser | Ser | Pro | Ile | Ile | Gly | Asn | Val | Gly | Pro | Thr | Met | Gly | Lys |
| 511> | Pro | Gly | Asn | Thr | Ile | Thr | Ile | Asp | Gly | Arg | Gly | Phe | Gly | Thr | Thr |
| 526> | Lys | Asn | Lys | Val | Thr | Phe | Gly | Thr | Thr | Ala | Val | Thr | Gly | Ala | Asn |
| 541> | Ile | Val | Ser | Trp | Glu | Asp | Thr | Glu | Ile | Lys | Val | Lys | Val | Pro | Asn |
| 556> | Val | Ala | Ala | Gly | Asn | Thr | Ala | Val | Thr | Val | Thr | Asn | Ala | Ala | Gly |
| 571> | Thr | Thr | Ser | Ala | Ala | Phe | Asn | Asn | Phe | Asn | Val | Leu | Thr | Ala | Asp |
| 586> | Gln | Val | Thr | Val | Arg | Phe | Lys | Val | Asn | Asn | Ala | Thr | Thr | Ala | Leu |
| 601> | Gly | Gln | Asn | Val | Tyr | Leu | Thr | Gly | Asn | Val | Ala | Glu | Leu | Gly | Asn |
| 616> | Trp | Thr | Ala | Ala | Asn | Ala | Ile | Gly | Pro | Met | Tyr | Asn | Gln | Val | Glu |
| 631> | Ala | Ser | Tyr | Pro | Thr | Trp | Tyr | Phe | Asp | Val | Ser | Val | Pro | Ala | Asn |
| 646> | Thr | Ala | Leu | Gln | Phe | Lys | Phe | Ile | Lys | Val | Asn | Gly | Ser | Thr | Val |
| 661> | Thr | Trp | Glu | Gly | Gly | Asn | Asn | His | Thr | Phe | Thr | Ser | Pro | Ser | Ser |
| 676> | Gly | Val | Ala | Thr | Val | Thr | Val | Asp | Trp | Gln | Asn |     |     |     |     |

13. The process in accordance with claim 1, wherein said recombinant DNA comprises the following DNA sequence:

| 10 | 20 | 30 | 40 | 50 | 60 |
|---|---|---|---|---|---|
| GCTGGAAATC | TTAA TAAGGT | AAACT TTACA | TCAGATG TTG | TCTATCAAAT | TGTAGTGGAT |
| 70 | 80 | 90 | 100 | 110 | 120 |
| CGAT TTGTGG | ATGGAAATAC | ATCCAA TAAT | CCGAGTGGAG | CATTATTTAG | CTCAGGATGT |
| 130 | 140 | 150 | 160 | 170 | 180 |
| ACGA ATTTAC | GCAAGTATTG | CGGTGGAGAT | TGGCAAGGCA | TA TCAAT AA | AAT TAACGAT |
| 190 | 200 | 210 | 220 | 230 | 240 |
| GGGTAT TTAA | CAGATATGGG | TGTGACAGCG | ATAT GGATTT | CTCAGCCTGT | AGAAAATGTA |
| 250 | 260 | 270 | 280 | 290 | 300 |
| TT TTCTGTGA | TGAATGATGC | AAGCGGTTCC | GCATCCTATC | ATGG TTATTG | GGCGCGCGAT |
| 310 | 320 | 330 | 340 | 350 | 360 |
| TTCAAAAAGC | CAAACCCGTT | TT TTGGTACC | CTCAGTGAT T | TCCAACGTTT | AGTTGATGCC |
| 370 | 380 | 390 | 400 | 410 | 420 |
| GCACATGCAA | AAGGAATAAA | GGTAATTATT | GAC TTTGCCC | CCAACCATAC | TTCTCCTGCT |
| 430 | 440 | 450 | 460 | 470 | 480 |
| TCAGAAACGA | AT CCT TCTTA | TATGGAAAAC | GGACGACTGT | ACGATAATGG | GACATTGCTT |
| 490 | 500 | 510 | 520 | 530 | 540 |
| GGCGGTTACA | CAAATGATGC | CAACATGTAT | T TTCACCA TA | ACGGTGGAAC | AACGTTTTCC |
| 550 | 560 | 570 | 580 | 590 | 600 |
| AGCTT AGAGG | ATGGGATTTA | TCGAAATCTG | TTTGACT TGG | CGGACCTTAA | CCATCAGAAC |
| 610 | 620 | 630 | 640 | 650 | 660 |
| CCTGT TA TTG | ATAGG TATTT | AAAAGATGCA | GTAAAAA TGT | GGA TAGATAT | GGGGATTGAT |
| 670 | 680 | 690 | 700 | 710 | 720 |
| GGTAT CCGTA | TGGATGCGGT | GAAGCACATG | CCGTTTG GAT | GGCAAAAATC | TCTGATGGAT |
| 730 | 740 | 750 | 760 | 770 | 780 |
| GAGAT TGATA | AC TATCGTCC | TGTCTTTACG | TT TGGGGAGT | GG TTTTTGTC | AGAAAATGAA |
| 790 | 800 | 810 | 820 | 830 | 840 |
| GTGGACGCGA | ACAATCAT TA | CTTTGCCAAT | GAAAGTGG AA | TGAGT TTGCT | CGAT TTTCGT |
| 850 | 860 | 870 | 880 | 890 | 900 |
| TTCGGACAAA | AGCTTCGTCA | AGTATTGCGC | AATAACAGCG | ATAAT TGGTA | TGGC TTTAAT |
| 910 | 920 | 930 | 940 | 950 | 960 |
| CAAATGATTC | AAGATACGGC | ATCAGCATAT | GACGAGGTTC | TCG ATCAAGT | AACAT TCATA |
| 970 | 980 | 990 | 1000 | 1010 | 1020 |
| GACAACCATG | AT ATGGATCG | GTT TATGATT | GACGGAGGAG | ATCCGCGCAA | GGTGGATATG |
| 1030 | 1040 | 1050 | 1060 | 1070 | 1080 |
| GCACTTGCTG | TA TTATTGAC | ATCCCGTGGC | GTACCGAA TA | T TTACTATGG | TACAGAGCAA |
| 1090 | 1100 | 1110 | 1120 | 1130 | 1140 |
| TACATGACCG | GTAACGGCGA | TCCAAACAAT | CGTAAGATGA | TGAGTTCATT | CAA TAAAAAT |
| 1150 | 1160 | 1170 | 1180 | 1190 | 1200 |
| ACTCGCGCGT | ATCAAGT GAT | TCAAAAACTA | TCT TCTCTCC | GACGAAACAA | TCCGGCGTTA |
| 1210 | 1220 | 1230 | 1240 | 1250 | 1260 |
| GCT TATGGTG | ATACGGAACA | GCGTTGGATC | AATGGCGATG | TG TATGTGT A | TGAGCGACAG |
| 1270 | 1280 | 1290 | 1300 | 1310 | 1320 |
| T TTGGCAAAG | ATG TTGTGTT | AGTT CGGGTT | AATCGT AGTT | CAAGCAGTAA | TTAC TCGATT |
| 1330 | 1340 | 1350 | 1360 | 1370 | 1380 |
| ACTGGC TTAT | TTACAGCTTT | ACCAGCAGGA | ACATATACGG | ATCAGCT TGG | CGGTC TTTTA |
| 1390 | 1400 | 1410 | 1420 | 1430 | 1440 |
| GACGGAAATA | CAA TTCAAGT | CGGTTCAAAT | GGATCAGT TA | ATGCATT TGA | CTTAGGACCG |
| 1450 | 1460 | 1470 | 1480 | 1490 | 1500 |
| GGGGAAGTCG | GTGTATGGGC | ATACAGTGCA | ACAGAAAGCA | CGCCAATTAT | TGGTCATGT T |
| 1510 | 1520 | 1530 | 1540 | 1550 | 1560 |
| GGACCGATGA | TGGGGCAAGT | CGGTCATCAA | GTAACCATTG | ATGGCGAAGG | ATTCGGAACA |
| 1570 | 1580 | 1590 | 1600 | 1610 | 1620 |
| AATACGGGCA | CTGTGAAGTT | CGGAACGACA | GCTGCCAATG | TTGTG TCT TG | GTCTAACAAT |
| 1630 | 1640 | 1650 | 1660 | 1670 | 1680 |
| CAAATCGTTG | TGGCTGTACC | AAATGTG TCA | CCAGGAAAAT | ATAATATTAC | CGTCCAATCA |
| 1690 | 1700 | 1710 | 1720 | 1730 | 1740 |
| TCAAGCGGTC | AAACGAGTGC | GGCTTATGAT | AAC TTTGAAG | TACTAACAAA | TGATCAAGTG |
| 1750 | 1760 | 1770 | 1780 | 1790 | 1800 |
| TCAGTGCGGT | TTGT TGTTAA | TAACGCGACT | ACCAATCTAG | GGCAAAA TAT | ATACATTG TT |
| 1810 | 1820 | 1830 | 1840 | 1850 | 1860 |
| GGCAACGTAT | ATGAGCTCGG | CAACTGGGAC | ACTAGTAAGG | CAATCGGTCC | AATGT TCAAT |
| 1870 | 1880 | 1890 | 1900 | 1910 | 1920 |
| CAAGTGGT TT | ACTCCTATCC | TACATGGTA T | ATAGATGTCA | GTGTCCCAGA | AGGAAAGACA |
| 1930 | 1940 | 1950 | 1960 | 1970 | 1980 |
| ATT GAGTT TA | AGT TTATTAA | AAAAGACAGC | CAAGGTAATG | TCACTTGGGA | AAGTGGTTCA |
| 1990 | 2000 | 2010 | 2020 | 2030 | 2040 |
| AATCATG T TT | ATACGACACC | AACGAATACA | ACCGGAAAAA | TTATAGTGGA | TTGGCAGAAC |

14. The process in accordance with claim 1, wherein said recombinant DNA comprises the following DNA sequence:

| Position | Sequence | Position | Sequence | Position | Sequence | Position | Sequence | Position | Sequence | Position | Sequence |
|---|---|---|---|---|---|---|---|---|---|---|---|
| 10 | TCCCCGGATA | 20 | CGAGCGTGAA | 30 | CAACAAGCTC | 40 | AAT TTTAGCA | 50 | CGGA TACGGT | 60 | T TACCAGATT |
| 70 | GTAACCGACC | 80 | GGTTTGTGGA | 90 | CGGCAAT TCC | 100 | GCCAACAACC | 110 | CGACCGGAGC | 120 | AGCCTTCAGC |
| 130 | AGCGATCA TT | 140 | CCAACCTGAA | 150 | GCTGTATTTC | 160 | GGGGGCGACT | 170 | GGCAGGGGAT | 180 | CACGAACAAA |
| 190 | ATCAACGACG | 200 | GCTATCTGAC | 210 | CGGAATGGGC | 220 | ATCACCGCCC | 230 | TCTGGA TCTC | 240 | GCAGCCGGTT |
| 250 | GAGAACATCA | 260 | CCGCCGTCAT | 270 | CAATTA TTCG | 280 | GGCGTCAACA | 290 | ATACAG CTTA | 300 | CC ACGGTTAC |
| 310 | TGGCCTCGCG | 320 | ACTTCAAGAA | 330 | GACCAATGCC | 340 | GCGTTCGGCA | 350 | GCTTCACCGA | 360 | CT TC TCCAAT |
| 370 | TTGATCGCCG | 380 | CAGCGCATTC | 390 | ACACAATATC | 400 | AAGGTAGT TA | 410 | TGGACTT TGC | 420 | ACCT AATCAC |
| 430 | ACCAACCCGG | 440 | CTTCGAGTAC | 450 | GGACCCCTCG | 460 | TTCGCCGAGA | 470 | ACGGCGCGCT | 480 | CTACAACAAC |
| 490 | GGAACGCTGC | 500 | TCGGCAAGTA | 510 | TAGCAACGAT | 520 | ACCGCCGGCC | 530 | TG TTCCACCA | 540 | CAATGGCGGC |
| 550 | ACCGAT TTC T | 560 | CGACGACTGA | 570 | AAGCGGTATC | 580 | TACAAGAACC | 590 | TGTACGATCT | 600 | CGCGGATATC |
| 610 | AATCAGA ACA | 620 | ACAACACCAT | 630 | CGACTCGTAT | 640 | CTCAAGGAAT | 650 | CGATCCAGCT | 660 | GTGGCTGAAT |
| 670 | CTCGGAGTCG | 680 | ACGGCATCCG | 690 | CTTCGACGCC | 700 | GTGAAGCATA | 710 | TGCCTCAGGG | 720 | CTGGCAGAAG |
| 730 | AGCTACG TCT | 740 | CGTCGATCTA | 750 | CAGCAGCGCC | 760 | AATCCGGTGT | 770 | TCACC TTCGG | 780 | TGAATGGTTC |
| 790 | CTCGGCCCCG | 800 | ACGAAATGAC | 810 | CCAGGACAAC | 820 | ATCAACTTCG | 830 | CGAATCAGAG | 840 | CGGCATGCAC |
| 850 | CTGCTG GACT | 860 | TTGCGTTTGC | 870 | GCAGGAAATC | 880 | CGTGAAGTGT | 890 | TCCGCGACAA | 900 | GTCGGAGACG |
| 910 | ATGACCGACC | 920 | TGAACTCGGT | 930 | GATCTCCAGC | 940 | ACCGGCTCCA | 950 | GCTATAA TTA | 960 | CATCAACAAC |
| 970 | ATGG TTACGT | 980 | TCATCGACAA | 990 | CCATGACATG | 1000 | GACCGCTTCC | 1010 | AGCAAGCCGG | 1020 | AGCGAGCACT |
| 1030 | CGCCCGACCG | 1040 | AGCAGGCTCT | 1050 | TGCGGTAACG | 1060 | CTGACTTCCC | 1070 | GCGGCGTTCC | 1080 | GGCAATCTAC |
| 1090 | TACGGTACAG | 1100 | AGCAA TATAT | 1110 | GACCGGCAAC | 1120 | GGCGACCCGA | 1130 | ACAACCGCGG | 1140 | CATGATGACC |
| 1150 | GGCTTCGATA | 1160 | CGAACAAGAC | 1170 | AGCGTACAAA | 1180 | GT GATCAAGG | 1190 | CGCTGGCTCC | 1200 | GCTTCGCAAG |
| 1210 | TCCAACCCGG | 1220 | CTCTCGCCTA | 1230 | CGGCTCGACG | 1240 | AC CCAGCGTT | 1250 | GGGTGAACAG | 1260 | CGACGTCTAC |
| 1270 | GTAT ATGAAC | 1280 | GCAAGTTCGG | 1290 | AAGCAACGTA | 1300 | GC T TTCGTTG | 1310 | CCGTCAACCG | 1320 | CAGCTCGACG |
| 1330 | ACTGCCT ATC | 1340 | CGATATCGGG | 1350 | AGCGC TTACT | 1360 | GC TCTGCCAA | 1370 | ACGGAACGTA | 1380 | TACCGACGTT |
| 1390 | CTCGGCGGCC | 1400 | TGC TTAATGG | 1410 | CAATT CAATT | 1420 | AC CGTTAACG | 1430 | GCGGCACGGT | 1440 | CAGCAA CTTT |
| 1450 | ACACT TGCAG | 1460 | CGGGCGGTAC | 1470 | GGCAGTCTGG | 1480 | CAGTACACGA | 1490 | CGACGAAATC | 1500 | CTCGCC GATT |
| 1510 | ATCGGCAACG | 1520 | TCGGCCCGAC | 1530 | TATGGGCAAG | 1540 | CCCGGCAACA | 1550 | CCATCACGAT | 1560 | CGACGGACGC |
| 1570 | GGCTT CGGTA | 1580 | CTACGAAGAA | 1590 | CAAAGTT ACT | 1600 | T TCGGTACGA | 1610 | CAGCCGTTAC | 1620 | CGGCGCGAAC |
| 1630 | ATCGTGAGCT | 1640 | GGGAAGATAC | 1650 | CGAAATCAAG | 1660 | GTCAAAG TTC | 1670 | CGAACGTGGC | 1680 | CGCCGGCAAC |
| 1690 | ACGGCCGTTA | 1700 | CGGTAACGAA | 1710 | CGCCGCCGGC | 1720 | ACTACCAGCG | 1730 | CAGCGTTCAA | 1740 | CAACT T TAAC |
| 1750 | GTACTGACTG | 1760 | CCGA TCAGGT | 1770 | CACTGTCCGC | 1780 | TTCAAAGTCA | 1790 | ACAATGCCAC | 1800 | CACGGCCCTG |
| 1810 | GGACAAAACG | 1820 | TCTACCTGAC | 1830 | CGGTAACGTC | 1840 | GCCGAGCTTG | 1850 | GCAACTGGAC | 1860 | AGCCGCCAAC |
| 1870 | GCAATCGGTC | 1880 | CGATGTACAA | 1890 | CCAGGTAGAA | 1900 | GCCAGCTATC | 1910 | CGAC TTGGTA | 1920 | CT TCGACGTC |
| 1930 | AGCGTTCCGG | 1940 | CCAACACGGC | 1950 | GCTGCAATTC | 1960 | AA GTTCATCA | 1970 | AAGTGAACGG | 1980 | CT CGACAGTG |
| 1990 | ACTTGGGAAG | 2000 | GCGGCAACAA | 2010 | CCACACCTTC | 2020 | ACCTCGCCTT | 2030 | CGAGCGGCGT | 2040 | TGCGACCGTA |
| 2050 | ACGGTCGATT | 2060 | GGCAGAAC | | | | | | | | |

* * * * *